United States Patent
Heukensfeldt Jansen

(10) Patent No.: US 11,918,390 B2
(45) Date of Patent: *Mar. 5, 2024

(54) METHODS AND SYSTEMS FOR MOTION DETECTION IN POSITRON EMISSION TOMOGRAPHY

(71) Applicant: GE Precision Healthcare LLC, Milwaukee, WI (US)

(72) Inventor: Floribertus P. Heukensfeldt Jansen, Ballston Lake, NY (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 197 days.

This patent is subject to a terminal disclaimer.

(21) Appl. No.: 17/453,148

(22) Filed: Nov. 1, 2021

(65) Prior Publication Data
US 2022/0047227 A1 Feb. 17, 2022

Related U.S. Application Data

(63) Continuation-in-part of application No. 16/732,250, filed on Dec. 31, 2019, now Pat. No. 11,179,128.

(51) Int. Cl.
*A61B 6/03* (2006.01)
*G01T 1/29* (2006.01)
*G06T 7/00* (2017.01)

(52) U.S. Cl.
CPC ............ *A61B 6/037* (2013.01); *G01T 1/2985* (2013.01); *G06T 7/0012* (2013.01); *G06T 2207/10104* (2013.01)

(58) Field of Classification Search
None
See application file for complete search history.

(56) References Cited

U.S. PATENT DOCUMENTS 8,569,706 B2 10/2013 Thiruvenkadam et al.
9,470,801 B2 * 10/2016 Ziv ..................... G06T 11/008
(Continued)

FOREIGN PATENT DOCUMENTS

WO 2014141256 A1 9/2014
WO 2016033458 A1 3/2016

OTHER PUBLICATIONS

Feng et al. ("Real-time data-driven rigid motion detection and correction for brain scan with listmode PET," 2016 IEEE Nuclear Science Symposium, Medical Imaging Conference and Room-Temperature Semiconductor Detector Workshop (NSS/MIC/RTSD), Oct. 19, 2017 (Year: 2017).*

(Continued)

*Primary Examiner* — Soo Shin
(74) *Attorney, Agent, or Firm* — McCoy Russell LLP

(57) ABSTRACT

Methods and systems are provided for medical imaging systems. In one embodiment, a method for a medical imaging system comprises acquiring emission data during a positron emission tomography (PET) scan of a patient, reconstructing a series of live PET images while acquiring the emission data, tracking motion of the patient during the acquiring by determining a per-voxel variation for selected voxels in a current live PET image of the series of live PET images, and outputting an indication of patient motion based on the per-voxel variation for the selected voxels in each live PET image. In this way, patient motion during the scan may be identified and compensated for via scan acquisition and/or data processing adjustments, thereby producing a diagnostic PET image with reduced motion artifacts and increased diagnostic quality.

18 Claims, 19 Drawing Sheets
(2 of 19 Drawing Sheet(s) Filed in Color)

(56) References Cited

U.S. PATENT DOCUMENTS

| | | | |
|---|---|---|---|
| 10,004,462 B2* | 6/2018 | Ernst | G06T 7/292 |
| 10,282,836 B2 | 5/2019 | Ravishankar et al. | |
| 10,610,186 B2 | 4/2020 | Kesner | |
| 11,179,128 B2* | 11/2021 | Heukensfeldt Jansen | A61B 6/037 |
| 2004/0227091 A1* | 11/2004 | LeBlanc | G01T 1/1642 |
| | | | 250/366 |
| 2008/0265166 A1* | 10/2008 | Shekhar | G01T 1/1647 |
| | | | 250/363.03 |
| 2008/0273785 A1 | 11/2008 | Kesner | |
| 2010/0260402 A1 | 10/2010 | Axelsson et al. | |
| 2010/0266099 A1 | 10/2010 | Busch et al. | |
| 2011/0116695 A1 | 5/2011 | Wollenweber et al. | |
| 2012/0052010 A1 | 3/2012 | Sorensen et al. | |
| 2012/0063567 A1* | 3/2012 | Smith | A61B 8/0825 |
| | | | 378/37 |
| 2012/0292534 A1* | 11/2012 | Geneser | A61N 5/1069 |
| | | | 250/492.1 |
| 2014/0193336 A1* | 7/2014 | Rousso | A61B 6/503 |
| | | | 600/431 |
| 2016/0163042 A1* | 6/2016 | Wollenweber | G06T 11/003 |
| | | | 382/131 |
| 2016/0247293 A1 | 8/2016 | Beylin et al. | |
| 2017/0332983 A1 | 11/2017 | Tai et al. | |
| 2020/0008707 A1 | 1/2020 | Li et al. | |
| 2020/0037976 A1 | 2/2020 | Shah et al. | |
| 2020/0155098 A1* | 5/2020 | Jones | A61B 6/4241 |
| 2023/0206441 A1* | 6/2023 | Zhong | G06T 7/0012 |
| | | | 382/128 |

OTHER PUBLICATIONS

Dawood, M. et al., "Respiratory gating in positron emission tomography: A quantitative comparison of different gating schemes," Medical Physics, vol. 34, No. 7, Jul. 2007, 11 pages.

Liu, C. et al., "Quiescent period respiratory gating for PET/CT," Medical Physics, vol. 37, No. 9, Sep. 2010, 7 pages.

Jin, X. et al., "List-mode Reconstruction for the Biograph mCT with Physics Modeling and Event-by-Event Motion Correction," Physics in Medicine and Biology, vol. 58, No. 16, Aug. 21, 2013, Available Online Jul. 29, 2013, 33 pages.

Janis, S. et al., "A Comparison of Amplitude-based and Phase-based Positron Emission Tomography Gating Algorithms for Segmentation of Internal Target Volumes of Tumors Subject to Respiratory Motion," Int J Radiat Oncol Biol Phys., Nov. 1, 2013, vol. 87, No. 3, 15 pages.

ISA United States Patent and Trademark Office, International Search Report Issued in Application No. PCT/US2016/049094, dated Nov. 10, 2016, WIPO, 2 pages.

ISA United States Patent and Trademark Office, Written Opinion Issued in Application No. PCT/US2016/049094, dated Nov. 10, 2016, WIPO, 6 pages.

* cited by examiner

METHODS AND SYSTEMS FOR MOTION DETECTION IN POSITRON EMISSION TOMOGRAPHY

CROSS-REFERENCE TO RELATED APPLICATIONS

The present application is a continuation-in-part of U.S. Non-Provisional patent application Ser. No. 16/732,250, entitled "METHODS AND SYSTEMS FOR MOTION DETECTION IN POSITRON EMISSION TOMOGRAPHY", and filed on Dec. 31, 2019. The entire contents of the above-listed application are hereby incorporated by reference for all purposes.

FIELD

Embodiments of the subject matter disclosed herein relate to non-invasive diagnostic imaging, and more particularly, to positron emission tomography (PET).

BACKGROUND

Positron emission tomography (PET) generates images that represent a distribution of positron-emitting radiotracer within a body of a patient, which may be used to observe metabolic processes in the body and diagnose disease. During operation of a PET imaging system, the patient is initially injected with the radiotracer, which emits positrons as it decays. Each emitted positron may travel a relatively short distance before encountering an electron, at which point an annihilation occurs. When a positron interacts with an electron by annihilation, the entire mass of the positron-electron pair is converted into two 511 keV gamma photons (also referred to as 511 keV events). The photons are emitted in opposite directions along a line of response (LOR). The annihilation photons are detected by detectors that are placed on both sides of the LOR, in a configuration such as a detector ring, as coincident events. Thus, during data acquisition, the detectors detect the coincident events, which reflect a distribution of the radiotracer in the patient's body. An image thus reconstructed from the acquired image data includes the annihilation photon detection information. Typically, the image is reconstructed upon completion of the data acquisition, and it may be unknown if the acquired data is adequate for producing a high-quality image until after the image is reconstructed.

BRIEF DESCRIPTION

In one embodiment, a method for a medical imaging system includes acquiring emission data during a positron emission tomography (PET) scan of a patient, reconstructing a series of live PET images while acquiring the emission data, tracking motion of the patient during the acquiring by determining a per-voxel variation for selected voxels in a current live PET image of the series of live PET images, and outputting an indication of patient motion based on the per-voxel variation for the selected voxels in each live PET image. In this way, patient motion during the PET scan can be accurately detected and compensated for, thereby reducing motion artifacts and increasing a diagnostic quality of a resulting PET image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will be better understood from reading the following description of non-limiting embodiments, with reference to the attached drawings, wherein below.

DETAILED DESCRIPTION

Figure 1:
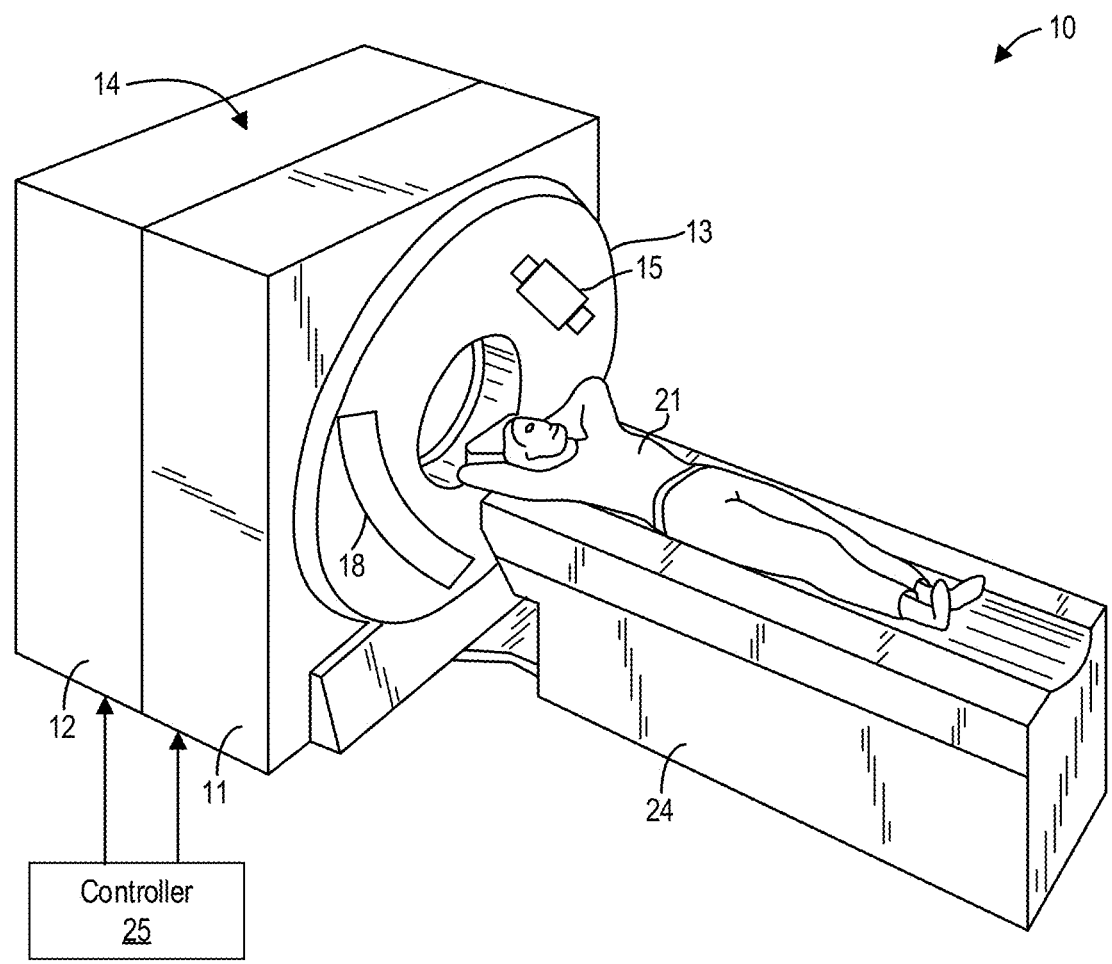
FIG. 1 shows a pictorial view of an exemplary multi-modality imaging system according to an embodiment of the disclosure.
Figure 2:
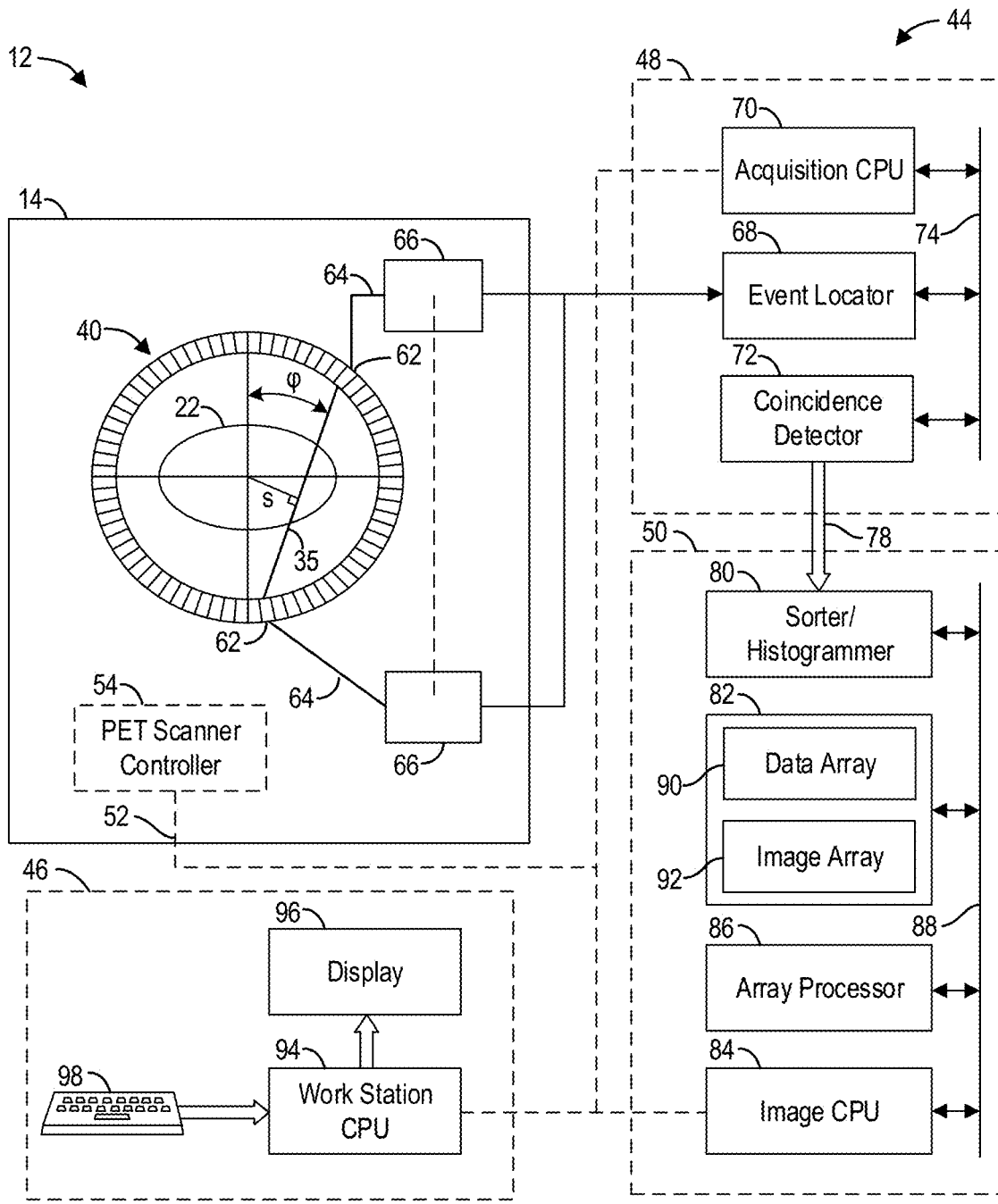
FIG. 2 shows a block schematic diagram of an exemplary positron emission tomography (PET) imaging system according to an embodiment of the disclosure.

The following description relates to various embodiments of medical imaging systems. In particular, methods and systems are provided for reconstructing positron emission tomography (PET) images in real-time for patient motion detection. An example of an imaging system that may be used to acquire images processed in accordance with the present techniques is provided in FIG. 1. Herein, the imaging system may be a multi-modality system. In one embodiment, the multi-modality imaging system may be a positron emission tomography/computed tomography (PET/CT) imaging system wherein a first modality is a CT imaging system and a second modality is a PET imaging system (as illustrated in FIGS. 1 and 2, for example). However, in other embodiments, the multi-modality imaging system may be a positron emission tomography/magnetic resonance imaging (PET/MRI) system wherein a first modality is a Mill system and a second modality is a PET imaging system.

When a patient is scanned using the PET imaging system, events captured within a field-of-view (FOV) of the imaging system may be used to reconstruct functional images of the patient. However, uncompensated patient motion during the scan may reduce the quality of resulting images. For example, image artifacts, blur, and increased noise may occur in the PET images due to patient motion during the scan, which may degrade a diagnostic value of the images. If a technologist operating the PET imaging system observes the patient moving, the technologist may issue instructions to the patient to remain still and extend a duration of the scan. Alternatively, the technologist may repeat the scan. However, because the technologist may not have a clear view of the patient within the imaging system, the technologist may be unaware that the patient is moving, resulting in degraded PET images or other hybrid modality images. In some examples, an inaccurate diagnosis may be made from the degraded images. In other examples, the degraded images may not be used, and a rescan may be requested. The rescan may include re-injecting the patient with radiotracer and repeating an entirety of the scan, which increases costs and patient discomfort and reduces imaging system availability.

Figure 3:
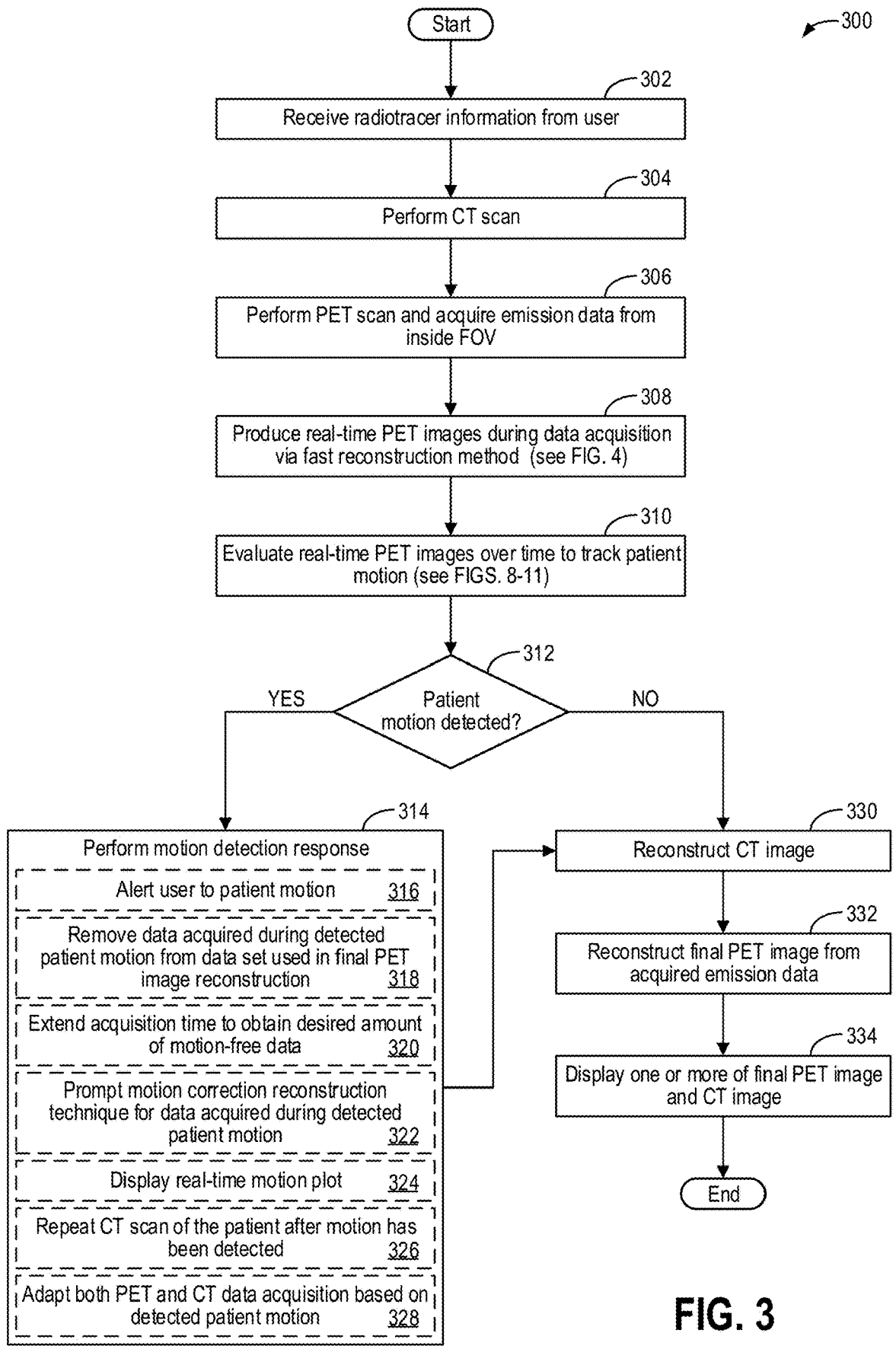
FIG. 3 shows a high-level flow chart of an example method for performing PET-computed tomography with real-time PET image reconstruction to detect and respond to patient motion, according to an embodiment of the disclosure.
Figure 4:
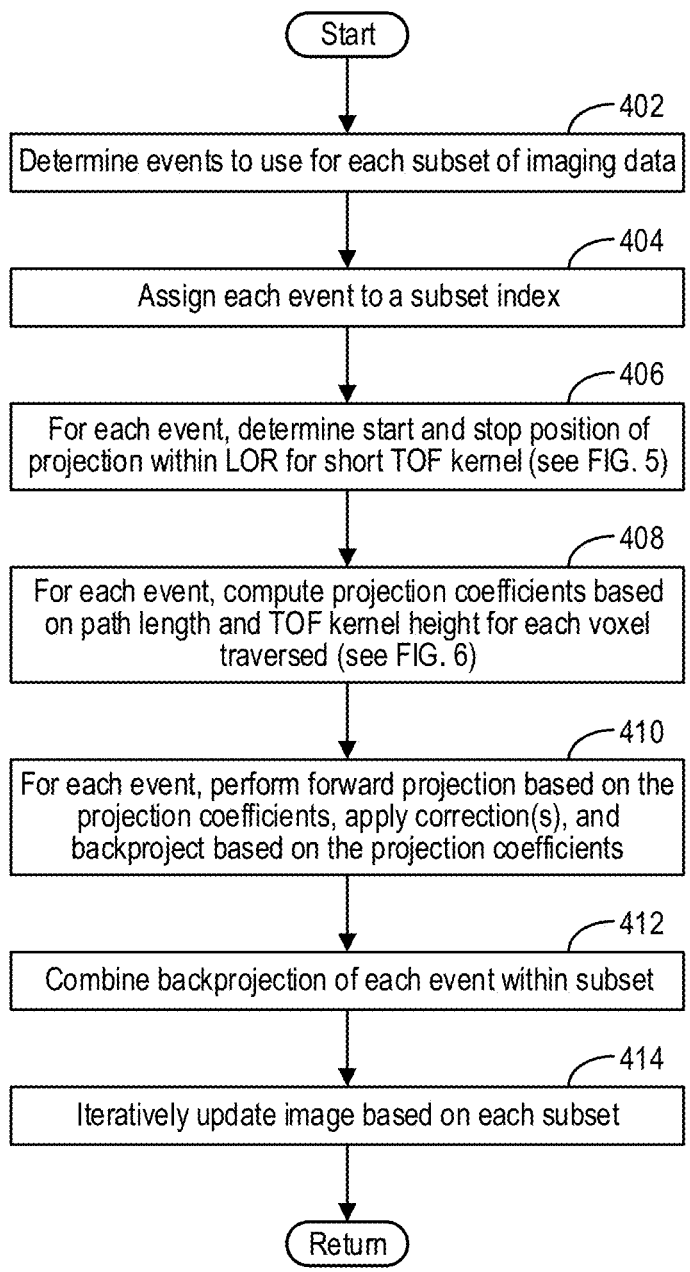
FIG. 4 shows a flow chart of an example method for reconstructing PET images in real-time for patient motion detection, according to an embodiment of the disclosure.
Figure 5:
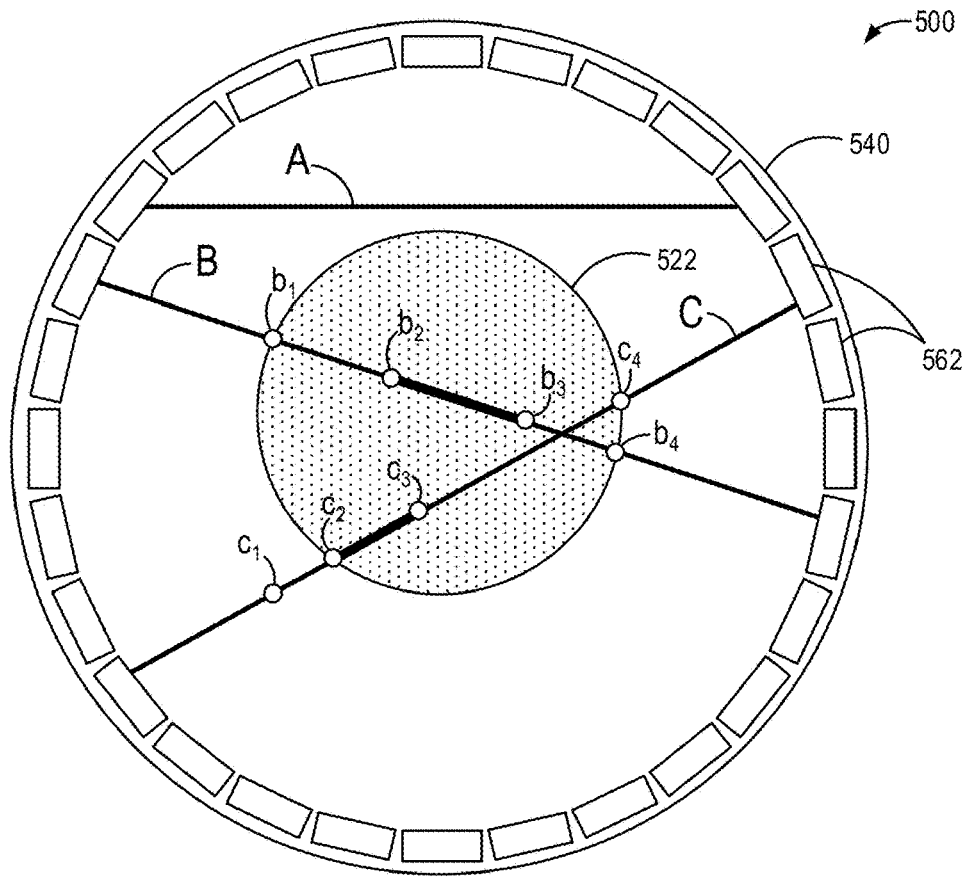
FIG. 5 schematically shows how segments may be selected on a line of response for real-time PET image reconstruction, according to an embodiment of the disclosure.
Figure 6:
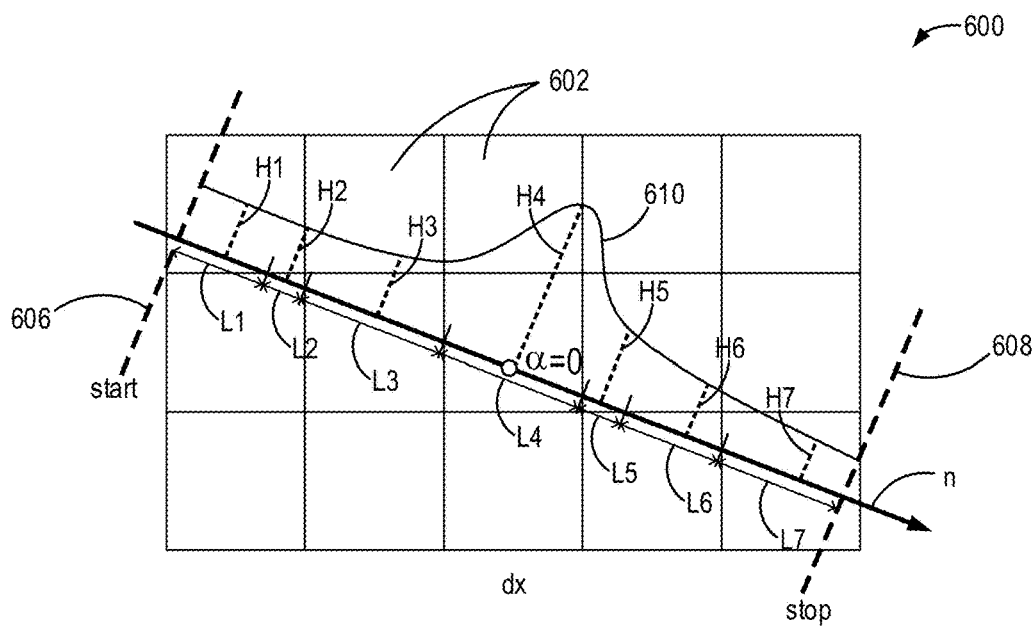
FIG. 6 schematically shows how projection weights may be determined for real-time PET image reconstruction, according to an embodiment of the disclosure.
Figure 7:
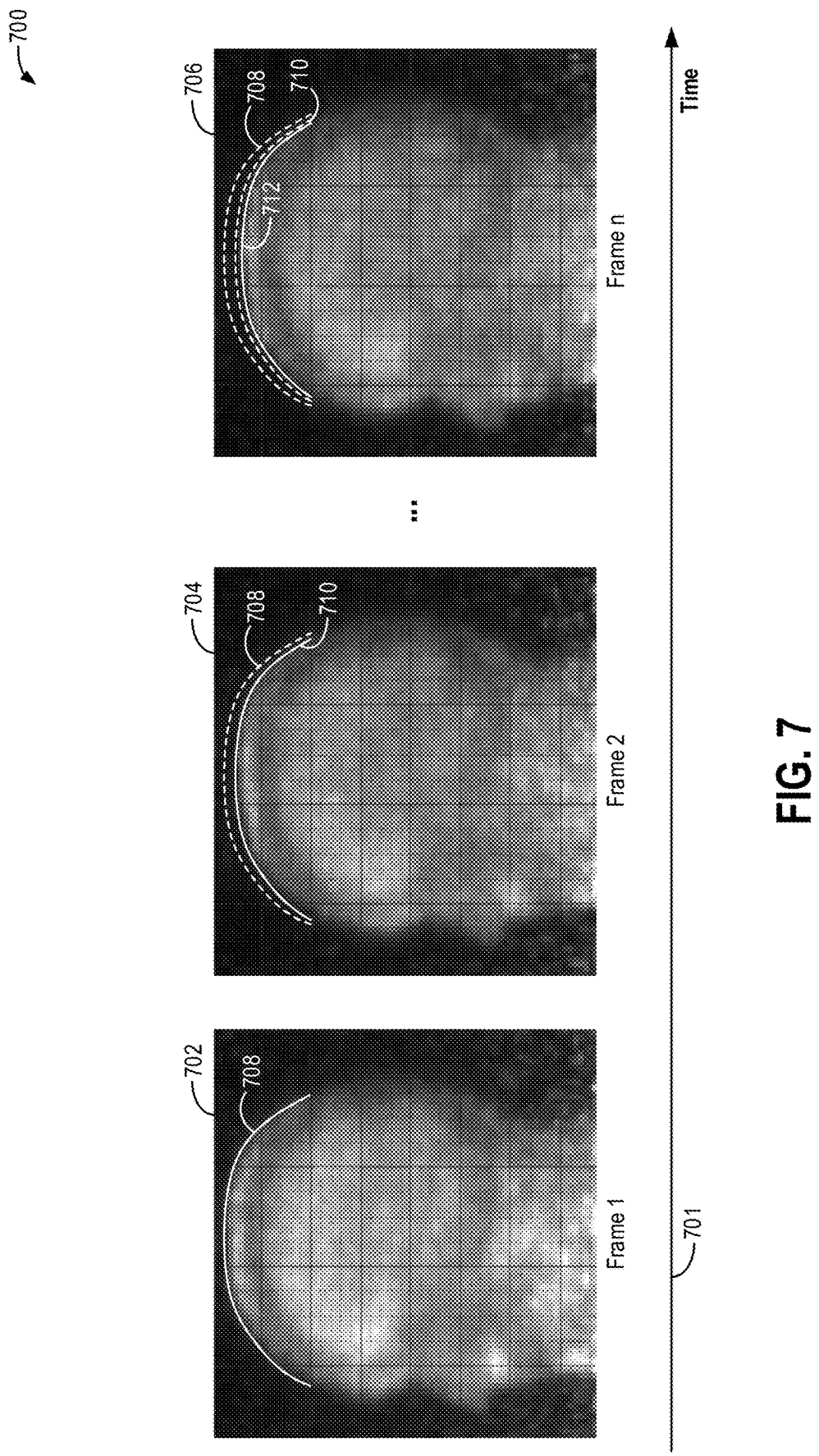
FIG. 7 shows an example of detecting patient motion during PET using PET images reconstructed in real-time.
Figure 13:
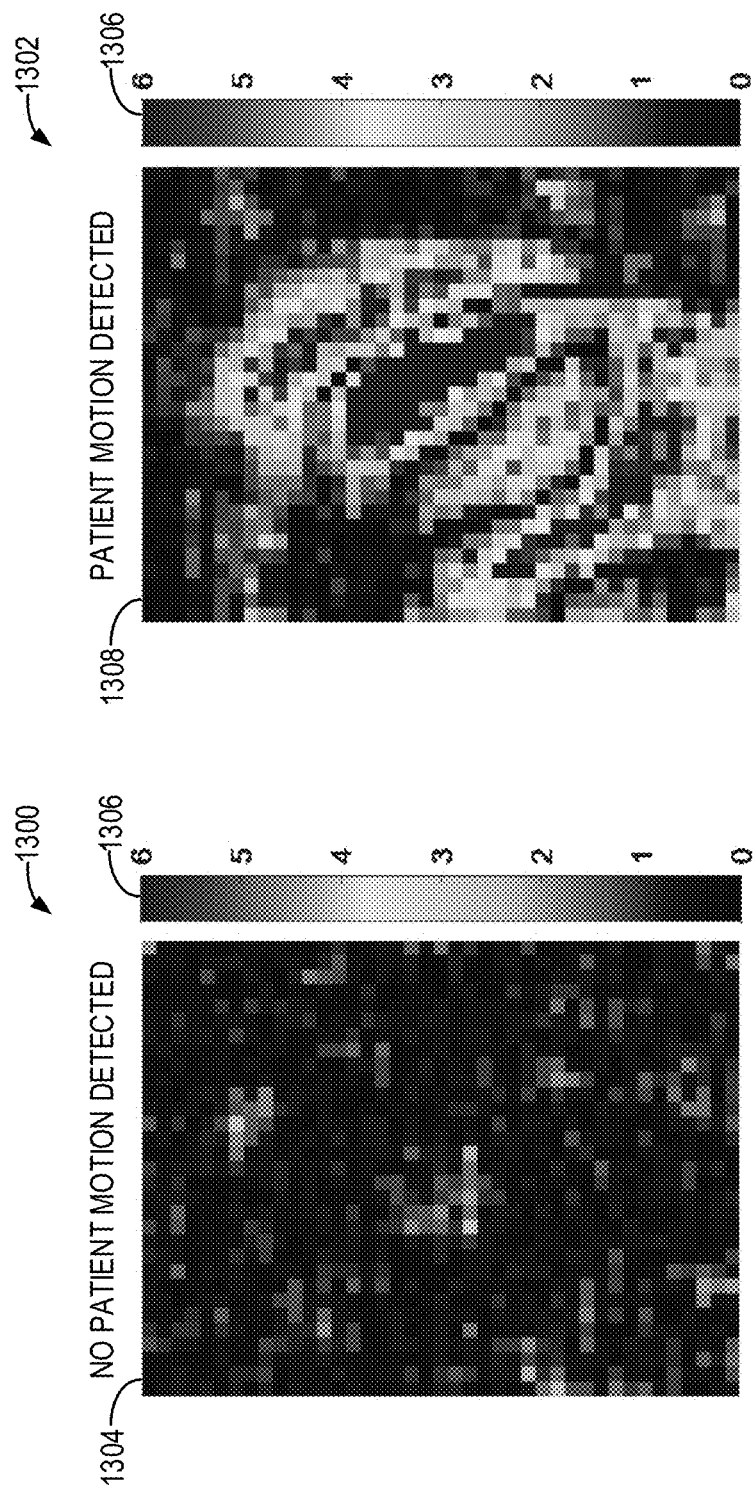
FIG. 13 shows an example map of z-scores when no patient motion is detected relative to when patient motion is detected in live PET images.
Figure 14:
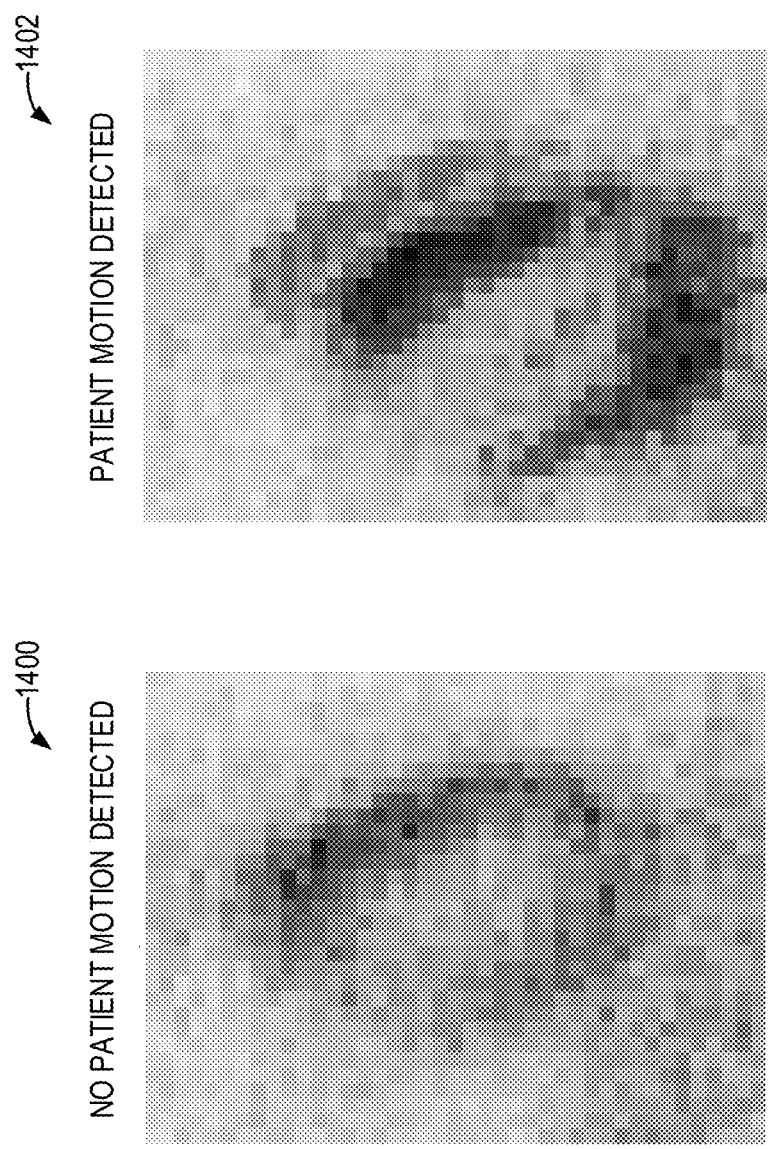
FIG. 14 shows example live PET images with patient motion indicated via a colorized image overlay.
Figure 19:
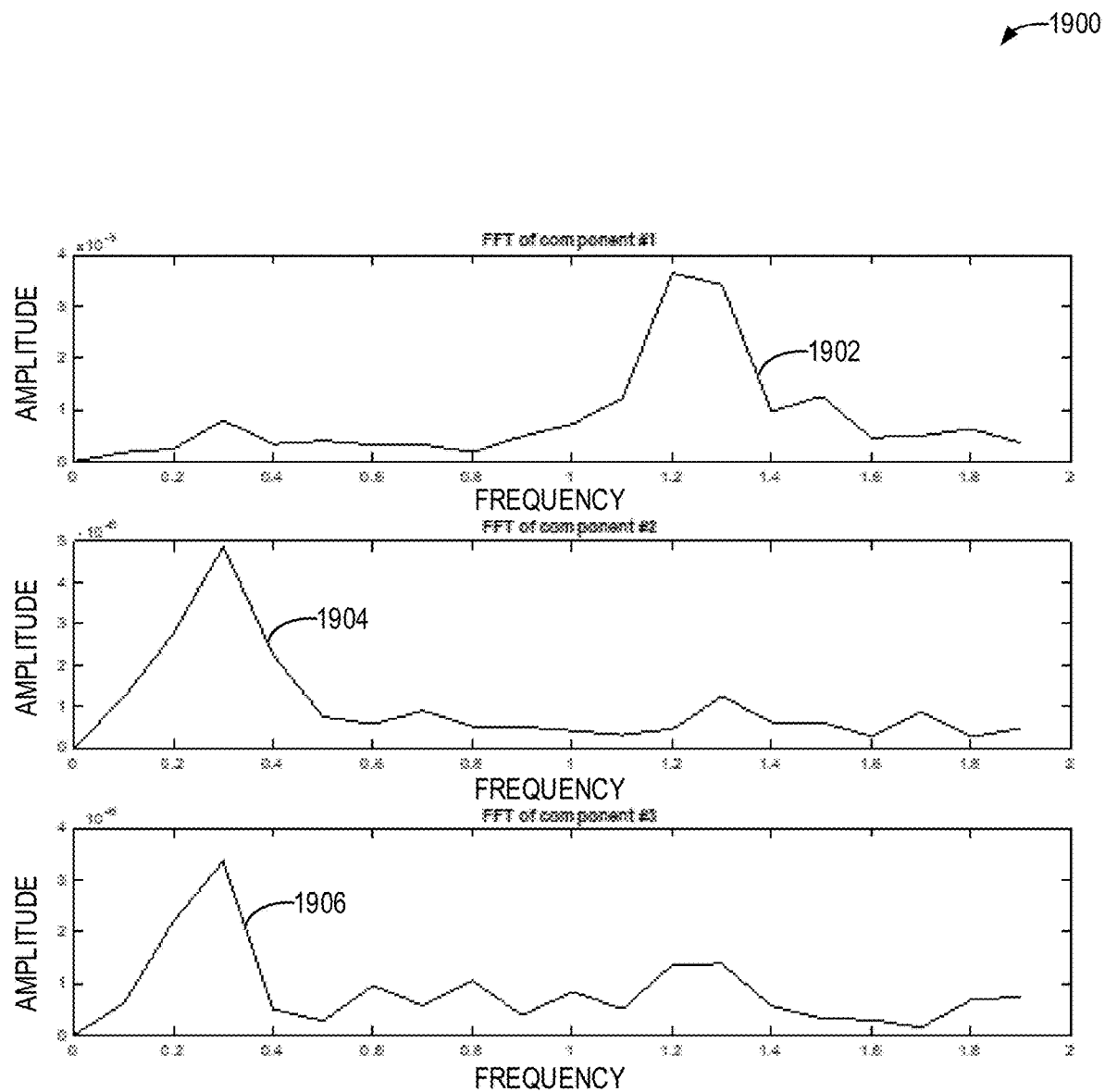
FIG. 19 shows a frequency analysis of components identified via a PCA that may be used to detect patient motion.
Figure 20:
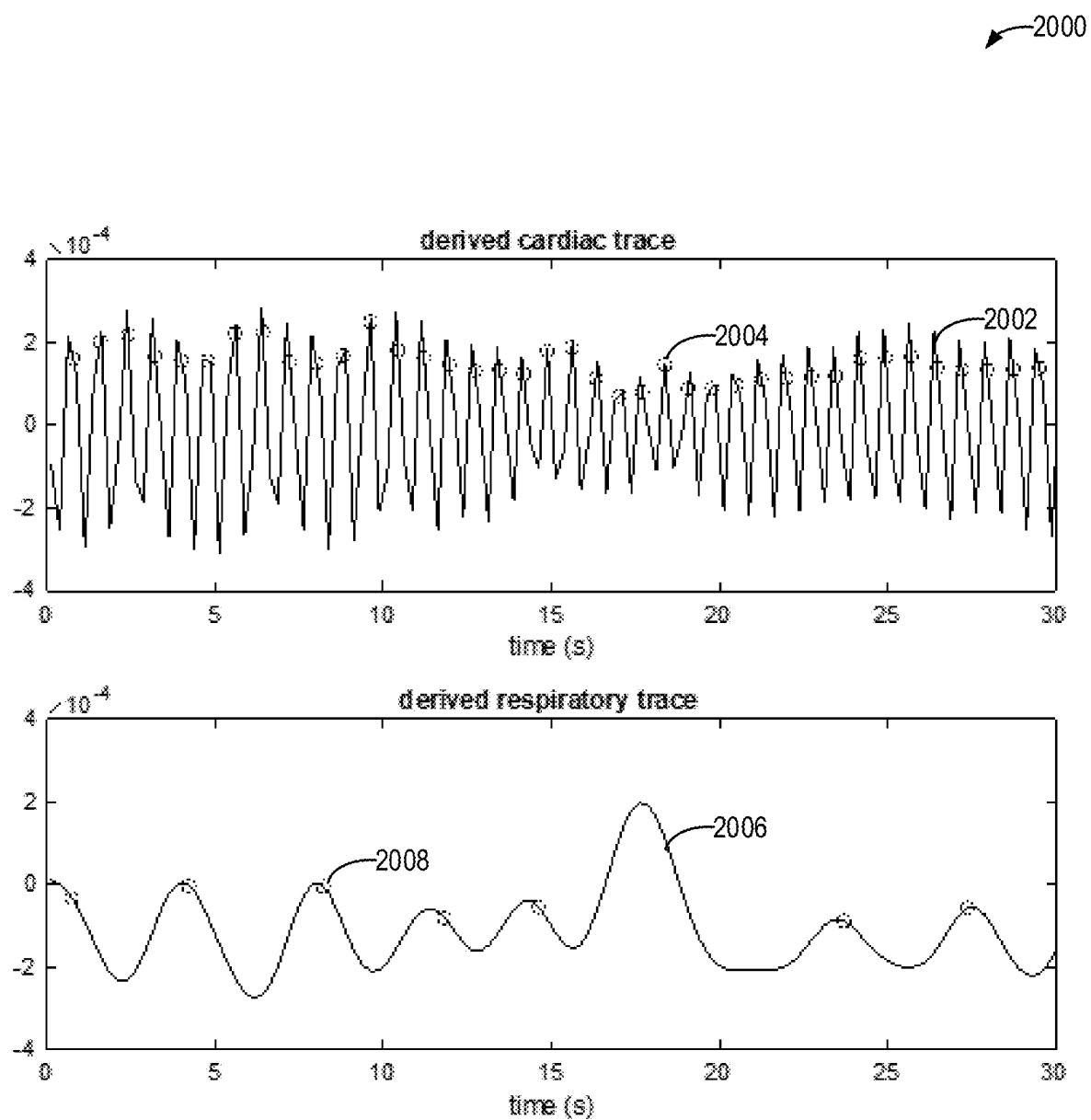
FIG. 20 shows cardiac and respiratory signals obtained through a PCA.

Therefore, an example method for detecting and tracking patient motion in the PET imaging system is shown in FIG. 3, which utilizes real-time PET images reconstructed using an example fast reconstruction method shown in FIG. 4. Herein, a list-mode reconstruction is performed on projection space data acquired during very short time frames, allowing manageable data sizes that can be processed in real-time to generate image space data. For example, time-of-flight (TOF) PET information may be leveraged in the fast reconstruction method to produce real-time PET images, such as shown in FIGS. 5 and 6. Image registration between the real-time PET images from different time frames may be used for patient motion analysis, an example of which is shown in FIG. 7. As another example, voxel-wise motion analysis may be performed to determine patient motion, such as according to the example methods of FIGS. 8-11. For example, a given frame may be compared to a reference determined from a quiescent period, such as according to the method of FIG. 8 and schematically shown in FIG. 12. As another example, a given frame may be compared to adjacent frames to detect patient motion, such as according to the method of FIG. 9. As yet another example, a given frame may be compared to a rolling mean of a number of frames to detect patient motion, such as according to the method of FIG. 10. As still another example, principal component analysis (PCA) may be used to detect patient motion, such as according to the method of FIG. 11. In such examples of voxel-wise motion analysis, patient motion may be output as an overlay on the real-time PET images, examples of which are shown in FIGS. 13 and 14, or output as a number of counts, various examples of which are shown in FIGS. 15-18. Further, when PCA is used to detect patient motion, a frequency analysis may enable periodic motion, such as respiratory and cardiac motion, to be more accurately identified, such as illustrated in FIGS. 19 and 20.

When the patient motion exceeds a threshold that will result in motion-related degradation in a final PET image used for diagnostics, which is different than the real-time PET images used for the motion detection, various motion detection responses may be employed. For example, a scan time may be selectively extended to capture additional motion-free data, data acquired during the patient motion may be discarded, advanced motion correction reconstruction techniques may be used on the data acquired during the patient motion during the final image reconstruction, etc. Further, in hybrid imaging modalities such as the PET/CT system shown in FIG. 1, CT data acquired prior to the detected patient motion may also be repeated. By addressing patient motion in real-time during a PET scan, imaging resources may be spent more efficiently, and scan costs may be decreased. Further, patient discomfort may be decreased. Further still, an amount of time before an accurate diagnosis is made may be decreased.

Though a PET/CT imaging system is described by way of example, it should be understood that the present techniques may also be useful when applied to images acquired using other imaging modalities, such as CT, tomosynthesis, MM, ultrasound, and so forth. The present discussion of a PET/CT imaging modality is provided merely as an example of one suitable imaging modality. In other examples, a PET/MRI imaging system or other imaging system including a PET imaging modality may be used.

As used herein, the phrase "reconstructing an image" is not intended to exclude embodiments of the present disclosure in which data representing an image is generated but a viewable image is not. Therefore, as used herein the term "image" broadly refers to both viewable images and data representing an estimate of the spatial distribution of emission activity as obtained by the reconstruction process. However, many embodiments generate, or are configured to generate, at least one viewable image.

Turning now to the figures, a multi-modality imaging system 10 is shown in FIGS. 1 and 2. Multi-modality imaging system 10 may be a suitable type of imaging system, for example, such as a Positron Emission Tomography (PET) imaging system, a Single Photon Emission Computed Tomography (SPECT) imaging system, a PET/Computed Tomography (CT) imaging system, a PET/ultrasound imaging system, a PET/Magnetic Resonance Imaging (MRI) system, or any other imaging system capable of generating tomographic images through PET. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects.

Referring first to FIG. 1, the multi-modality imaging system 10 includes a first modality unit 11 and a second modality unit 12. The two modality units enable the multi-modality imaging system 10 to scan an object or patient in a first modality using the first modality unit 11 and in a second modality using the second modality unit 12. The multi-modality imaging system 10 allows for multiple scans in different modalities to facilitate an increased diagnostic capability over single modality systems. In the embodiment shown in FIG. 1, multi-modality imaging system 10 is a Positron Emission Tomography/Computed Tomography (PET/CT) imaging system 10. In the present example, the first modality unit 11 is a CT imaging system 11, and the second modality unit 12 is a PET imaging system 12. The PET/CT system 10 is shown as including a gantry 13 (or a first gantry portion) included in the CT imaging system 11 and a gantry 14 (or a second gantry portion) included in the PET imaging system 12. For example, the CT imaging system 11 may generate anatomical images of a patient, while the PET imaging system 12 may generate functional images corresponding to the distribution of a radiotracer as a marker of physiological processes such as metabolism. As discussed above, modalities other than CT and PET may be employed with the multi-modality imaging system 10.

The gantry 13 includes an x-ray source 15 that projects a beam of x-ray radiation (or x-rays) for use in imaging a patient 21 positioned on a motorized table 24. Specifically, the x-ray source 15 is configured to project the x-ray radiation beams toward a detector array 18 positioned on the opposite side of the gantry 13. Although FIG. 1 depicts only a single x-ray source 15, in certain embodiments, multiple x-ray sources and detectors may be employed to project a plurality of x-ray radiation beams for acquiring projection data at different energy levels. In some embodiments, the x-ray source 15 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. In still other examples, multiple x-ray sources may emit the same energy for faster scanning, such as during cardiac applications. It should thus be appreciated that the methods described herein may be implemented with single energy acquisition techniques as well as dual energy acquisition techniques.

In certain embodiments, the CT imaging system 11 further includes a controller or processor 25 configured to reconstruct images of a target volume of the patient 21 using an iterative or analytic image reconstruction method. For example, the controller or processor 25 may use an analytic image reconstruction approach such as filtered back projection (FBP) to reconstruct images of a target volume of the patient. As another example, the controller or processor 25 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient 21. In some embodiments, the controller or processor 25 may use a direct image reconstruction approach, such as using deep-learning trained neural networks. As described further herein, in some examples the controller or processor 25 may use an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during a partial revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, PET, or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved with continuous axial motion along the main axis of the scanner while the data for the prescribed number of slices is acquired. Such a system generates a single helix from a cone beam helical scan. The helix mapped out by the cone beam yields projection data from which images in each prescribed slice may be reconstructed.

In certain embodiments of the multi-modality imaging system 10, the controller or processor 25 may be configured to operate both the CT imaging system 11 and the PET imaging system 12. In other embodiments, the CT and the PET imaging systems may each include a dedicated controller that separately controls the CT and the PET imaging systems.

Continuing to FIG. 2, a block schematic diagram of the PET imaging system 12 introduced in FIG. 1 is shown. The PET imaging system 12 includes a detector ring assembly 40 including a plurality of detectors (or detector crystals) 62. For example, the detector ring assembly 40 may be positioned in the gantry 14. Further each of the detectors 62 includes one or more crystals (e.g., a scintillation crystals) and one or more photo sensors. In another example, the detectors 62 may each include one or more avalanche photodiodes, photomultipliers, silicon photomultipliers, and/or another type of radiation detector. The PET imaging system 12 also includes a controller or processor 44 configured to control normalization and image reconstruction processes. Controller 44 is operatively coupled to an operator workstation 46. In one non-limiting example, the controller 44 may be an example of the controller 25 of FIG. 1. As another example, the controller 44 may be included in (e.g., a part of) or communicatively connected to controller 25 of FIG. 1, such as via wired or wireless communication. In the example of FIG. 2, controller 44 includes a data acquisition processor 48 and an image reconstruction processor 50, which are interconnected via a communication link 52. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 21, may be positioned using, for example, the motorized table 24 (shown in FIG. 1). The motorized table 24 is aligned with a central axis of detector ring assembly 40. The motorized table 24 moves the patient 21 into the central opening of detector ring assembly 40 in response to one or more commands received from the operator workstation 46. A PET scanner controller 54, also referred to as the PET gantry controller, is provided (e.g., mounted) within PET imaging system 12. The PET scanner controller 54 responds to the commands received from the operator workstation 46 through the communication link 52. Therefore, the scanning operation may be controlled from the operator workstation 46 through PET scanner controller 54.

Prior to a PET scan, a radioactive nuclide (e.g., radionuclide), or radiotracer, is delivered to the patient 21. For example, the radionuclide may be fluorine-18, carbon-11, nitrogen-13, oxygen-15, or the like and may be injected into the patient 21. The radionuclide may be incorporated into a molecule that is normally metabolized by the body or into a molecule that binds to a receptor target, for example. As such, the radionuclide accumulates within organs, vessels, or the like. The radionuclide undergoes positron emission decay and thereby emits a positron, which collides with an electron in the surrounding tissue. The positron encounters an electron and, when the positron collides with an electron, both the positron and the electron are annihilated and converted into a pair of photons, or gamma rays, each having any energy of 511 keV. The two photons are directed in substantially opposite directions and are each detected when they reach respective detectors 62 positioned across from each other on the detector ring assembly 40. Thus, the two detectors 62 detecting the coincident scintillation events are positioned substantially 180 degrees from each other relative to the point of annihilation. When the photon collides with the detector, it produces a scintillation event (e.g., flash of light) on the detector crystal. Each photosensor of the respective detector 62 detects the scintillation event and produces a signal that is transmitted on a communication line 64. A set of acquisition circuits 66 receive the signals from the photosensor via the communication line 64. Acquisition circuits 66 produce digital signals indicating the three-dimensional (3D) location and total energy of the event. The acquisition circuits 66 also produce an event detection pulse, which indicates the time or moment the scintillation event was detected. These digital signals are transmitted through a communication link, for example, a cable, to an event locator circuit 68 in the data acquisition processor 48.

The data acquisition processor 48 includes the event locator circuit 68, an acquisition CPU 70, and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each event and provides a set of digital numbers or values indicative of the detected event. For example, this information indicates when the event took place and the position of the detector 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, time markers in each event data packet must be within a predetermined time period, such as within 5 nanoseconds of each other, to indicate coincidence. Second, a line-of-response (LOR) 35 formed by a straight line joining the two detectors that detect the coincidence event should pass through a field of view (FOV) 22 in the PET imaging system 12. Events that cannot be paired are discarded. Coincident event pairs are located and recorded as a coincidence data packet that is communicated through a communication link 78 to a sorter/histogrammer 80 in the image reconstruction processor 50.

The image reconstruction processor 50 includes the sorter/histogrammer 80. During operation, the sorter/histogrammer 80 generates a data structure known as a histogram. The histogram includes a large number of cells, where each cell corresponds to a unique pair of detectors crystals in the PET imaging system 12. Because a PET imaging system typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient 21. The completed histogram containing all data from the scan is commonly referred to as a "result histogram." The term "histogrammer" generally refers to the components of the controller 44, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each parallel LORs at an angle φ and forms a projection. For example, a line integral along all of the parallel LORs at angle φ and a distance s from a center of the FOV 22 forms a projection p(s, φ). The projections for all angles are further organized into a data array 90. The data array 90 may be a sinogram, which is a function of s and φ. A single projection fills one row in the sinogram, and the sinogram includes a superposition of all projections weighted by an average count at each point. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of an image array 92. Resulting image arrays 92 are then stored in memory module 82.

The images stored in the image array 92 are communicated by the image CPU 84 to the operator workstation 46. The operator workstation 46 includes a CPU 94, a display 96, and an input device 98. The CPU 94 connects to communication link 52 and receives inputs, e.g., user commands, from the input device 98. The input device 98 may be, for example, a keyboard, mouse, a touch-screen panel, and/or a voice recognition system. Through input device 98 and associated control panel switches, the operator can control the operation of the PET imaging system 12 and the positioning of the patient 21 for a scan. Similarly, the operator can control the display of the resulting image on the display 96 and can perform image-enhancement functions using programs executed by the workstation CPU 94.

Further, in some examples, a timing precision for detecting the 511 keV events may be high enough that the coincidence detector 72 is able to measure a time-of-flight (TOF) difference between the two photons. For example, when a positron annihilation event occurs closer to a first detector crystal than a second detector crystal, one annihilation photon may reach the first detector crystal before (e.g., nanoseconds or picoseconds before) the other annihilation photon reaches the second detector crystal. The TOF difference may be used to constrain a location of the positron annihilation event along the LOR, which may increase an accuracy and quality the image reconstructed by the image reconstruction processor 50. A resolution of the TOF difference, or TOF kernel, may be a predetermined value stored in a memory of the controller 44 or may be determined based on, for example, a count rate. The same TOF kernel may be used for analyzing all of the LORs in a dataset, for example.

Note that the various components and processes of controller 44 described above are provided as one example of how controller 44 may obtain, process, and store data generated during operation of PET imaging system 12. In other examples, controller 44 may include different processors and memories with similar or different functionalities to those described above in similar or different arrangements. In particular, controller 44 may employ parallel or massively parallel processing. Further, in some embodiments, various processors of controller 44, such as the data acquisition processor 48 and the image reconstruction processor 50, may be contained within a shared housing, while in other embodiments, the various processors of controller 44 may be contained within separate housings that are in a same or a different location. Thus, in some examples, the processors of controller 44 may span multiple locations that are communicatively connected.

During PET, such as when a PET imaging system (e.g., PET imaging system 12 of FIGS. 1 and 2) of a medical imaging facility is operated to image a patient (e.g., patient 21 FIGS. 1 and 2), the patient may move. Motion can lead to blurring of the data, increased noise, reduced quantitative accuracy, and an introduction of image artifacts. As a result, a diagnostic value of the obtained images may be degraded. A technologist operating the PET imaging system may be unaware that the patient has moved and thus may not take steps to address the patient motion. In some examples, the obtained imaging data may undergo substantial motion correction post-imaging, which uses a large amount of computation resources. However, even when the post-imaging motion correction is used, the diagnostic value of the images may still be degraded, which may lead to misdiagnosis or a rescan of the patient being ordered. Even if the patient is immediately available at the medical imaging facility, the previously used radionuclide may be unusable due to isotope decay. As a result, the patient may be reinjected with the radionuclide before the scan is repeated. If the patient (or a second dose of the radiotracer) is not immediately available, the patient may have to return to the medical imaging facility for the rescan. Overall, an amount of time before a diagnostic is made, patient discomfort, and an imaging cost all may be increased.

Therefore, FIG. 3 provides an example method 300 for tracking motion of a patient within an imaging system during a scan based on PET images that are reconstructed in real-time. Method 300 will be described for a PET/CT imaging system, such as imaging system 10 described with respect to FIGS. 1-2, although other PET imaging systems may be used. Instructions for carrying out method 300 and the rest of the methods included herein may be executed by a controller (e.g., controller 25 of FIG. 1 and/or controller 44 of FIG. 2) based on instructions stored on a memory of the controller and in conjunction with signals received from sensors of the imaging system, such as the sensors described above with reference to FIGS. 1-2. The controller may employ actuators of the imaging system to adjust the operation of the imaging system according to the methods described below.

At 302, method 300 includes receiving radiotracer information from a user (e.g., technologist) of the imaging system. Receiving the radiotracer information from the user includes a type of radiotracer that is injected into the patient positioned within the imaging system. The radiotracer may be a positron-emitting radionuclide. Some non-limiting examples of radiotracers include fluorine-18 fludeoxyglucose (FDG), carbon-11 choline, nitrogen-13 ammonia, and oxygen-15 water. In some examples, the type of radiotracer injected may depend on an anatomy of interest that is being imaged. As mentioned above, the radiotracers injected into the patient may accumulate within organs, vessels or the like and begin to decay and emit positrons. As explained previously, the positrons annihilate, generating a pair of gamma rays. In addition to the type of tracer injected, the controller may receive additional information, such as a time of injection, a dose of radiotracer injected, and a pre-injection delay. In addition to radiotracer information, the controller may receive a weight of the subject. In one example, the user may enter the weight of the patient. As another example, the controller may additionally receive a selected imaging protocol, which may be selected by the user or manually input by the user.

At 304, method 300 includes performing the CT scan. As one example, performing the CT scan may include first performing a CT scout scan. The CT scout scan may serve as an anatomical reference for the PET/CT scan. In one example, the CT scout scan may be used to define starting and ending locations for the CT and PET acquisitions. In some examples, the CT scout scan may be a whole body scan. Once the starting and ending locations are defined, the method includes acquiring additional CT image data within the region defined by the starting and the ending locations. For example, CT image data may be acquired by activating an x-ray source (e.g., x-ray source 15 of FIG. 1) according to specified parameters, which may be input by the user or specified by the imaging protocol selected by the user (e.g., a specified kV, mA, attenuation filter position). Further, a gantry (e.g., gantry 13 of FIG. 1) may be rotated to achieve the specified angles. Further, during the CT scan, the position of a table of the imaging system (e.g., table 24 of FIG. 1) may be moved such that the scan progresses from the start scan location to the stop scan location.

At 306, method 300 includes performing the PET scan and acquiring emission data from inside a field of view (FOV) of the imaging system. The PET scan may generate functional images corresponding to dynamic occurrences such as metabolism. To perform the PET scan and acquire the emission data, detector crystals of the PET imaging system are activated to detect gamma rays emitted from the patient due to positron emission and annihilation, and acquisition circuits, event locator circuits, and a coincidence detector may together record coincidence events, as elaborated above with respect to FIG. 2.

At 308, method 300 includes producing real-time PET images during the data acquisition via a fast reconstruction method. As will be elaborated below with respect to FIGS. 4-6, in some examples, the fast reconstruction method may not use all of the emission data obtained for each image reconstruction in order to provide the real-time (e.g., without significant delay) PET images. As such, the real-time PET images include a series of live images that represent the emission data being acquired as it is acquired (e.g., at the time of occurrence, with only a sub-second or second time delay). For example, some of the data may be skipped and/or discarded by the fast reconstruction method. As another example, the real-time, fast reconstruction method additionally or alternatively may utilize subsetting to reduce processing times. Further, the fast reconstruction method may not employ attenuation or scatter correction, as the images produced may be used to determine patient position and may not be used for diagnostics, for example. Further still, the fast reconstruction method may not employ motion correction.

The fast reconstruction method may use TOF list-mode reconstruction (instead of sinogram-based reconstruction). As such, the controller may not organize the emission data into a histogram prior to the reconstruction (e.g., sorter/histogrammer 80 of FIG. 2 may not be used). The list-mode data includes a list of all the detected coincidence events. Each item in the list identifies the two detector crystals involved, a difference in detected times between the two detector crystals (e.g., TOF information, as described above with respect to FIG. 2), and an indication of an absolute time that the coincidence was detected. The controller may evaluate image values corresponding to the approximate location of the coincidence based on the LOR between the two detector crystals and the difference in time that the events were detected for each item in the list. After a group (e.g., subset or iteration) of events are processed, an update to the image can be applied. The number of image updates applied may vary from one update to a plurality of updates. Increasing the number of image updates may provide a statistically optimal image at the expense of increasing reconstruction time, for example.

The fast reconstruction method may reconstruct image volumes for short time frames (e.g., time periods) to produce the real-time PET images. For example, each short time frame may include a pre-defined duration of time, which may range from milliseconds to seconds. As one non-limiting example, each short time frame is one second each. In such an example, the pre-defined duration may be used to determine (or define) the event data to include for each time frame. As another example, the duration of each time frame may vary based on a number of events captured. For example, the duration may be adjusted in order to acquire a desired number of events (e.g., 4 million). The time frame may extend until the desired number of new events are detected, and then the subsequent time frame may commence. In such an example, the number of events may be used to determine (or define) the event data to include for each time frame as well as the duration of each time frame.

One real-time (e.g., live) PET image may be reconstructed from the emission (e.g., event) data obtained during one time frame, and each real-time, live PET image may be referred to herein as an "image frame." In some examples, the time frames may be contiguous and non-overlapping, while in other examples, the time frames may partially overlap such that a subsequent time frame starts before a preceding time frame ends. As one example, a first time frame may begin, and the data acquired during the first time frame may be reconstructed via the fast reconstruction method upon completion of the first time frame (e.g., the pre-determined duration or the desired number of detected events). While the real-time PET image is produced for the first time frame, data may be collected for a second, subsequent time frame. This sequence may be repeated iteratively throughout the scan to produce a series of real-time PET images.

As one example, the series of real-time PET images may include image frames reconstructed at pre-determined time points, each time point separated by a pre-selected interval (e.g., the pre-defined duration of time) and each image frame reconstructed from the emission data acquired during the immediately preceding interval. In this way, one image frame may be reconstructed every one second, for example. As another example, the series of real-time PET images may include image frames reconstructed after acquiring a pre-determined amount of data. In this way, one image frame may be reconstructed every n event acquisitions, for example.

As a further example, the image frames may be reconstructed from partially overlapping sets of data. For example, consecutive image frames may share a percentage of events in a range from 30-70%, the percentage of events corresponding to a proportion of total events used for reconstructing each consecutive image frame that are shared by the consecutive image frames. In one non-limiting example, successive image frames may share a 50% overlap in events. For example, one image frame may be reconstructed from event 1 through N, where N is a predetermined number, and the next image frame may be reconstructed from event N/2+1 through 3N/2 for a 50% overlap of events between successive frames. However, the data sets used for reconstructing consecutive image frames may be overlapped in other ways.

Alternatively, if a count rate of events is very high, the number of events detected per second may be too great for all of them to be used in real-time reconstruction. As will be elaborated below with respect to FIG. 4, in such an example, not all of the detected events may be used in reconstructing the image frame in order to maintain the real-time performance of the system. For example, if the count rate of events is 10 million per second and the controller is capable of reconstructing 4 million per second, then the controller may not use the events after the first 4 million, reconstruct an image frame with the first 4 million events, and resume collecting events at the start of the next second. However, the controller may continue to store all list events for subsequent (non real-time) processing. In this way the real-time reconstruction may be maintained regardless of the event count rate.

Because the time frame is short, a number of coincidence events in the emission data obtained during the time frame is relatively small, and by using the TOF data, only a small portion of the image is considered for each detected coincidence. As such, the list-mode reconstruction is more efficient than a sinogram-based reconstruction for the same emission data.

Further, the real-time PET images may be reconstructed using an efficient randoms calculation. A random event refers to the detection of two photons that meet criteria for coincidence that are not actually from a same positron annihilation event (e.g., the coincidence is random). Randoms are a source of image degradation in PET and may be compensated for during or before image reconstruction. As one example, a singles map may show a count rate in individual detectors. Instead of computing randoms from an expansion of the singles map into a full sinogram, which uses over 400 million calculations, for the fast reconstruction method, a simple multiplication may be used. For example, a randoms rate (R) for a LOR between detector crystals i and j may be calculated using a singles rate (SR method) according to the equation:

$$R = 2S_i S_j \tau$$

where $S_i$ is a singles count of the detector crystal i, $S_j$ is a singles count of the detector crystal j, and $\tau$ is a timing window for detecting coincidence. As such, the randoms calculation may be performed using fewer computational resources. Similar principles may be applied for normalization and deadtime. By including randoms and normalization in the real-time PET image reconstruction, image quality may be increased, which may aid the motion detection described below.

At 310, method 300 includes evaluating the real-time PET images over time to track patient motion. For example, registration may be performed on each image frame as it is reconstructed, such as by transforming each image frame onto a unified coordinate system. The unified coordinate system may provide a reference for comparing the image frames to each other. In real-time, each newly reconstructed and registered image frame may be compared with the immediately preceding (e.g., previously reconstructed) image frame (or a pre-determined number of preceding image frames) in the series to determine whether or not the patient has moved between image frames with respect to the unified coordinate system. As such, method 300 may provide real-time motion computation from image space.

The registration may be performed using one or more algorithms. In some examples, the registration algorithm(s) may utilize edge detection to define boundaries of the patient's anatomy in each image frame and may further use change detection to determine if the boundaries defined by the edge detection have moved with respect to the unified coordinate system over time (e.g., between image frames), as will be elaborated with respect to FIG. 7. For example, the edge detection may provide rigid registration and may be used when an anatomical feature being imaged is a rigid body, such as the head. However, the registration algorithm(s) may additionally or alternatively utilize other transformations and analysis methods that enable a comparison of the patient position between image frames. For example, the controller may perform non-rigid registration between image frames, such as by using an optical flow approach. The optical flow approach may create a full 3D motion field, showing how each element of a volume has moved as compared to a reference frame (e.g., an initial time point). Further, the registration algorithm(s) may determine an absolute magnitude of the motion based on a displacement of the patient (or a displacement of one or more boundaries) between image frames, for example.

In other examples, real-time motion detection may be performed using other algorithms that do not perform image registration. For example, image registration may be relatively slow compared with methods that detect a variation per-voxel. Example methods will be described below with respect to FIGS. 8-11. For example, the voxels in each image frame may be compared to a background noise reference that is generated from a quiescent period during the imaging, as will be describe with reference to FIG. 8. As another example, adjacent frames may be used to detect voxel-wise variation, as will be elaborated with respect to FIG. 9, or using a rolling mean image of a desired number of frames, such as described with respect to FIG. 10. As yet another example, artificial intelligence may be used to estimate the background noise reference. As still another example, principal component analysis may be used to evaluate periodic motion, such as described with reference to FIG. 11. Further still, in some embodiments, a combination of image registration and voxel-wise motion analysis methods may be used for the real-time motion detection.

At 312, method 300 includes determining if patient motion is detected. For example, patient motion may be detected when the absolute magnitude of the motion exceeds a pre-determined motion threshold stored in a memory of the controller. The motion threshold may be calibrated to differentiate smaller changes in the patient position from larger changes in the patient position. For example, the smaller changes may be more accurately compensated for using post-imaging motion correction algorithms than the larger changes. As another example, the larger changes in the patient position may not be accurately corrected via processing or may warrant more complex processing than the smaller changes in the patient position. For example, when the absolute magnitude of the motion exceeds the motion threshold, image quality degradation may occur. Conversely, patient motion having an absolute magnitude below the motion threshold may be corrected without degrading the image quality. Patient motion below the motion threshold may be caused by the patient breathing, for example. The magnitude of the motion may refer to a variation of the patient between image frames, such as a displacement of the patient, a rotation of the patient, and/or another characteristic that indicates a statistically significant mismatch in the patient position between image frames.

As still another example, the controller may determine a degree of similarity in the overall patient position in two image frames, and the controller may indicate patient motion is detected responsive to the degree of similarity decreasing below a threshold degree of similarity. The threshold degree of similarity may differentiate the smaller changes in the patient position from the larger changes in the patient position defined above.

When the variation is determined on a per-voxel basis, the motion threshold may be a number of voxels that are over a threshold variation. The threshold variation may be used to differentiate variation that occurs due to, for example, shallow breathing and cardiac motion from variation that occurs due to deep breaths, the patient changing their pose, etc., as will be elaborated below with respect to FIG. 8. Thus, even if several voxels have variations over the threshold variation, patient motion may not be detected if the number of voxels experiencing the variation is less than the motion threshold. As such, the motion threshold may differentiate movements that may not impact the quality of the final PET images, such as shallow breathing and cardiac motion, from movements that may result in motion artifacts.

If patient motion is not detected, method 300 proceeds to 330 and includes reconstructing a CT image. One or more CT images may be reconstructed using, as a non-limiting example, an analytic reconstruction algorithm, such as filtered back projection or an iterative reconstruction algorithm.

At 332, method 300 includes reconstructing a final PET image from the acquired emission data. In particular, the final PET image may be completed after all of the emission data has been acquired (e.g., after the PET scan is complete). As such, the final PET image is not a real-time representation of the acquired emission data (e.g., the final PET image is a non-live PET image). In some examples, the final PET image may be reconstructed using emission data spanning an entire duration of the data acquisition. In other examples, such as the examples that will be noted further herein, a portion of the data may be selectively excluded. In some examples, the final PET image may include one cross-sectional image of the patient. In other examples, the final PET image may include multiple cross-sectional images of the patient. Further, because a large number of coincidence events may be used in reconstructing the final PET image relative to the number of coincidence events used in reconstructing the real-time PET images, a sinogram-based reconstruction may be performed. For example, the sinogram-based reconstruction may more efficiently process the larger data set than the list-mode reconstruction described above with respect to the real-time PET images. Therefore, the sinogram-based reconstruction will be described below. However, in other examples, list-mode reconstruction may be used for reconstructing the final PET image.

As explained previously with reference to FIG. 2, an image reconstruction processor of the PET imaging system may include a sorter/histogrammer (such as sorter/histogrammer 80 of FIG. 2). The sorter/histogrammer includes a histogram of a large number of bins, where each bin corresponds to a unique pair of detector crystals. Each bin of the histogram also stores a count value representing the number of coincidence events detected by the pair of detector crystals for that bin during the scan, which may be organized into a sinogram. After all of the data is acquired for a particular patient location and the PET scan is no longer actively being performed at that patient location, the data in the histogram is used to reconstruct the final PET image of the patient. For example, the total number of coincidence events detected by the pair of detector crystals will be proportional to an amount of radiotracer within the LOR connecting the pair. The final PET image may be used by a clinician for diagnostic purposes, whereas the real-time PET images may not be used for diagnostics.

The controller may use analytic and/or iterative image reconstruction algorithms. Analytic reconstruction algorithms may provide a direct mathematical solution for the reconstructed image, whereas iterative image reconstruction algorithms may use multiple mathematical iterations to arrive at the reconstructed image. Further, the controller may employ attenuation and/or scatter correction in reconstructing the final PET image. For example, various scatter correction methods, such as model-based scatter simulation, may be used to estimate scattered events during PET image reconstruction. The model-based scatter simulation uses knowledge of the emission activity and attenuation coefficients and may include both single scatter and multiple scatter estimation. The emission activity may be estimated by an initial PET image reconstruction using the acquired PET data within the FOV.

At 334, method 300 includes displaying one or more of the final PET image and the CT image. The one or more images may be displayed on a display screen, such as display 96 of FIG. 2, for example. As mentioned above, the CT image may define anatomical structures, whereas the PET image may show dynamic bodily functions, such as metabolism. As also mentioned above, the radiotracer injected into the subject may accumulate in organs. An increased uptake of the radiotracer in an organ may therefore appear as a "hot spot" in the PET image. Abnormal tissue (or tumors) may have increased uptake and hence appear as hot spots in the PET image. However, normal tissues also uptake different levels of the radiotracer. For example, a radiotracer such as FDG is cleared primarily through the renal system, and thus a normal bladder may have a greatest amount of FDG update. The brain may have a higher FDG uptake than the adipose tissue, for example. The radiotracer uptake by normal tissues may be physiological, whereas radiotracer uptake by abnormal tissues may be pathological. Thus, the final PET image may provide functional information to aid in diagnostics.

In some examples, the CT image and the final PET image may be superimposed (e.g., via co-registration) in order to put the functional information from the PET image into the anatomical context given by the CT image. These views may allow the clinician to correlate and interpret information from the two different imaging modalities on one image, which may result in more precise information and more accurate diagnoses. Method 300 may then end.

Returning to 312, if instead patient motion is detected, such as in response to the absolute magnitude of the motion exceeding the threshold motion, method 300 proceeds to 314 and includes performing a motion detection response. For example, the controller may indicate that patient motion is detected via an internal condition that initiates a motion detection response and/or indicate an alert to the user. The controller may select one or more motion detection responses from a plurality of possible motion detection responses and perform the selected response(s) simultaneously or sequentially. Further, the controller may identify the time frame(s) over which the patient motion (or variation) exceeds the threshold in order to apply the selected motion detection responses accordingly.

Performing the motion detection response optionally includes alerting the user to the patient motion, as indicated at 316. For example, the controller may output an audible and/or visual alert to the user via a workstation, such as operator workstation 46 of FIG. 2. As one example, the alert may notify the user that patient motion is detected and may further prompt the user to instruct the patient to remain still. Additionally or alternatively, the controller may output an image indicating the motion, such as via an image overlay, map, or plot of voxels that are over the threshold variation, as will be elaborated below with respect to FIGS. 8-15.

Performing the motion detection response additionally optionally includes removing data acquired during the detected patient motion from a data set to be used in the final PET image reconstruction, as indicated at 318. For example, the data acquired while the patient motion is greater than the threshold may be separated from data acquired while the patient motion is not greater than the threshold, and only the data acquired while the patient motion is not greater than the threshold may be used in reconstructing the final PET image. Removing the data acquired during the detected patient motion may be performed in addition to or as an alternative to outputting the alert at 316. By segregating the data acquired during the detected motion from the data set to be used for the final PET image reconstruction, the data acquired during the detected patient motion may be excluded from the final PET image. As such, motion artifacts due to the detected patient motion will not be present in the final PET image.

Performing the motion detection response optionally includes extending an acquisition time of the scan to obtain a desired amount of motion-free data, as indicated at 320. For example, the desired amount of motion-free data may be a pre-determined count number or data acquisition duration during which the patient motion remains below the threshold. The pre-determined count number or data acquisition duration may be calibrated values stored in a memory of the controller and may represent a minimum amount of desired data for achieving a final PET image with reduced noise and image artifacts. Extending the acquisition time of the scan may be performed in addition to or as an alternative to one or both of outputting the alert at 316 and removing the data acquired during the detected motion at 318.

Performing the motion detection response optionally includes prompting use of a motion correction reconstruction technique for data acquired during the detected patient motion, as indicated at 322. The motion correction technique may not be performed automatically, as it may be computationally expensive. Therefore, at least in some examples, the motion correction technique may be selectively applied to the data acquired while the patient motion is greater than the threshold instead of the entire data set. As another example, the motion correction technique may be selectively applied to the data acquired while the patient motion is indicated as well as the data acquired after the indicated patient motion. As an illustrative example, the patient motion may result in the patient moving from a first pose to a second pose. Although the patient may not actively move while in the second pose (e.g., the patient motion remains less than the threshold while in the second pose), all of the events acquired while the patient is in the second pose may be corrected in order to compensate for differences between the first pose and the second pose. Further, in some examples, the emission data may be segregated into "before motion," "during motion," and "after motion" data sets, which may be at least partially processed separately from one another in order to accurately correct for the patient motion while increasing computational efficiency. Prompting the use of the motion correction reconstruction technique may be performed in addition to or as an alternative to any or all of outputting the alert at 316, removing the data acquired during the detected motion at 318, and extending the acquisition time of the scan at 320. By performing the motion correction technique, the data acquired during the detected patient motion may still be used in the final PET image reconstruction without introducing blur and motion artifacts, for example.

Performing the motion detection response optionally includes displaying a real-time motion plot, as indicated at 324. For example, the real-time motion plot may show patient displacement within the FOV over time in the three spatial directions, which may be displayed to the user via the display screen. Because the user may be unable to see the patient motion within the gantry, the real-time motion plot may allow the user to more easily monitor the movement of the patient during the scan. As another example, additionally or alternatively, the real-time motion plot may show the number of voxels having a variation that is greater than the threshold variation, which may be shown as a function of frame number or a function of time. An example of such a real-time motion plot will be described below with respect to FIG. 15. Displaying the real-time motion plot may be performed in addition to or as an alternative to any or all of outputting the alert at 316, removing the data acquired during the detected motion at 318, extending the acquisition time of the scan at 320, and prompting the use of the motion correction reconstruction technique at 322.

Performing the motion detection response optionally includes repeating the CT scan of the patient after motion has been detected, as indicated at 326. For example, new CT image data may be acquired by activating the x-ray source while the gantry is rotated to achieve the angles specified by the imaging protocol. The new CT image data may replace the earlier CT image data, which may be discarded or temporarily stored separated from the new CT image data until the CT image is reconstructed. Repeating the CT scan may be performed in addition to or as an alternative to any or all of outputting the alert at 316, removing the data acquired during the detected motion at 318, extending the acquisition time of the scan at 320, prompting the use of the motion correction reconstruction technique at 322, and displaying the real-time motion plot at 324.

Although motion detection during the PET scan may not directly correlate to patient motion during the CT scan, repeating the CT scan may increase a likelihood that motion-free and correctly registered CT scan data is obtained. However, in other hybrid imaging modalities in which data is acquired for the two modalities simultaneously, such as in PET/MRI, the detected motion affects both imaging modalities. As such, the method at 326 may include selectively repeating MR scan portions performed during the detected patient motion (and not repeating the entire MR scan, for example).

Performing the motion detection response optionally includes adapting both the PET and CT data acquisition based on the detected patient motion, as indicated at 328. For example, the PET and CT data acquisition may be extended in order to capture additional motion-free data. Extending the PET and CT data acquisition when patient motion is detected (and not when patient motion is not detected) may enable the imaging system resources to be more efficiently used while also increasing the image quality of both the final PET image and the CT image. Adapting both the PET and the CT data acquisition based on the detected patient motion may be performed in addition to or as an alternative to any or all of outputting the alert at 316, removing the data acquired during the detected motion at 318, extending the acquisition time of the scan at 320, prompting the use of the motion correction reconstruction technique at 322, displaying the real-time motion plot at 324, and repeating the CT scan at 326.

Method 300 proceeds to 330 and includes reconstructing the CT image, as described above. Thus, the CT image may be reconstructed after additional data is acquired and/or compensations are performed for the detected patient motion. As a result, the CT image may have fewer motion artifacts, and the image quality may be increased.

The final PET image reconstructed at 332 may also have increased image quality compared with not performing the selected motion detection response(s). For example, the data acquired during the patient motion may not be used for reconstructing the final PET image (e.g., when selected at 318), thereby reducing blur and noise in the final PET image while increasing a quantitative accuracy of the final PET image. As another example, the motion correction reconstruction technique may be applied to the data acquired during the patient motion (e.g., when selected at 322), and the corrected data acquired during the patient motion may be used for reconstructing the final PET image without introducing blur and noise.

By tracking patient motion in real-time (or near real-time) using the fast reconstruction method, various adjustments and adaptations to the imaging protocol may be made in real-time in order to compensate for the patient motion and/or exclude data obtained during the patient motion without negatively affecting image quality or scanner resources. In this way, PET images may be obtained with fewer motion artifacts, increasing a quality of the PET images and a diagnostic accuracy of the PET images. Further, CT images also may be reconstructed from data obtained while the patient is not moving, increasing the quality and accuracy of the CT images. Overall, an occurrence of patient rescans may be decreased while a quantitative accuracy of the final PET images may be increased, reducing imaging costs and a time to diagnosis.

Continuing to FIG. 4, an example method 400 for the fast reconstruction method introduced in FIG. 3 is shown. For example, method 400 may be performed by the controller as a part of method 300 of FIG. 3 (e.g., at 308) in real-time during PET data acquisition. At least parts of method 400 may be performed as one iteration of an image update for a single image frame, and multiple iterations may be performed in parallel for the single image frame, at least in some examples.

At 402, method 400 includes determining events to use for each subset of imaging data. For each short time frame described above at 308 for reconstructing real-time PET images (e.g., image frames), subsetting may be used to reach convergence more quickly. Instead of iterating over all events acquired during the time frame for every update of the image frame, every $n^{th}$ event may be used (where n is an integer), and n passes may be made over the data using a different subset of the events for each pass. Each pass may comprise one update, for example.

Therefore, in some examples, the controller may determine the value of n for determining the events to use for each subset. The value of n may be determined based on a data density and matrix size of the data set, for example, in order to maintain at least a lower threshold number of events in each subset. The lower threshold number of events may be a pre-determined value stored in memory that corresponds to an event number below which there is not enough data to produce an accurate image update. The controller may input the data density and the matrix size into a look-up table or algorithm, which may output the value of n for the given data set. The controller may then determine the events to use for each subset of the imaging data based on the determined value of n, such as by creating a look-up table of events to use for a given subset. As an illustrative example, when n is 4, a first iteration may use event 1, 5, 9, 13, etc.; a second iteration may use events 2, 6, 10, 14, etc.; a third iteration may use events 3, 7, 11, 15, etc.; and a fourth iteration may use events 4, 8, 12, 16, etc. In this way, a more converged image may be reached more quickly, with four updates to the image after processing each event just once, as will be further elaborated below. However, in some examples, as the time frame decreases, the number of events is smaller, and the data set cannot be broken into subsets (e.g., n is equal to 1).

In some examples, when the number of events captured in each time frame is higher than an upper threshold number of events, the controller may choose to skip events in order to reduce processing time. The upper threshold number of events may be a pre-calibrated value stored in memory that corresponds to an event number above which an anticipated processing time is greater than a pre-determined threshold duration for real-time processing. In some examples, the controller may adjust (e.g., increase) the value of n determined above and then only process a fraction of the subsets. Continuing the above illustrative example where n is 4, n may be increased to 5, and only 4 of the 5 subsets may be processed, for example, resulting in a 20% decrease in the processing time. As another example, additionally or alternatively, the total number of events in the data set may be decreased prior to determining the events for each subset. As an illustrative example, only the first 4 million events may be selected from 5 million total events, which may impart a slight time bias on the result.

In some examples, the controller may update the lower threshold number of events and/or the upper threshold number of events by measuring an actual time taken to process a data set of a given size. In this way, the controller may refine the fast reconstruction method as it is implemented in order to ensure generation of real-time PET images that provide accurate and timely patient motion detection.

At 404, method 400 includes assigning each event to a subset index. For example, the events in a single subset may be divided into groups or blocks of events, which may be stored in contiguous memory. The contiguous memory may undergo parallel processing, with each parallel thread assigned to process one block of events. For example, each parallel thread may access only one block of the given subset of the imaging data stored therein, reducing an amount of data processed by each thread. Further, at a start of each image update (e.g., each iteration), each thread gets its own copy of an update matrix so that the threads do not interfere with each other. When the threads have all completed their individual processing tasks, which are outlined below (e.g., from 406 to 410), their matrices are joined together before being applied to a single image update associated with that subset, which may be stored in the contiguous memory or in non-contiguous memory.

At 406, method 400 includes, for each event, determining a start position and a stop position of a projection within a line of response (LOR) for a short time-of-fight (TOF) kernel. Using the parallel processing described above, the controller may find the start position and the stop position for each coincident event in the given subset of data that travels through the imaging FOV, for example. As mentioned above with respect to FIG. 2, the TOF kernel may be standardized across the dataset so that the same TOF kernel is used for each LOR. Thus, the TOF kernel may define a shortest valid segment to project for a given LOR. As another example, using segments longer than the TOF kernel may result in increased processing times. Therefore, the controller may determine the start position and the stop position of each projection using the position of the TOF kernel on the LOR, which may further be determined from a timing difference between detecting each photon of an event.

Turning briefly to FIG. 5, a diagram 500 shows an illustrative example of determining how the start position and the stop position of the projection for different lines of response. FIG. 5 shows a detector ring assembly 540 of a PET imaging system, including a plurality of detectors 562. For example, the detector ring assembly 540 may be the detector ring assembly 40 of FIG. 2, and the plurality of detectors 562 may be the plurality of detectors 62 of FIG. 2. Diagram 500 also shows a PET imaging field of view (FOV) 522. The FOV 522 may include a patient positioned within the detector ring assembly 540, for example.

Three lines of response are shown in diagram 500: a first line A, a second line B, and a third line C. Line A does not cross the FOV 522. Therefore, no projection is determined for line A. Line B and line C each cross the FOV 522, and the detected events for each line are determined to be coincident (e.g., as determined by coincidence detector 72 of FIG. 2). Four points are computed for line B, including b1, b2, b3, and b4. The point b1 is where line B enters the FOV 522, the point b2 is where a TOF kernel starts for line B, the point b3 is where the TOF kernel ends for line B, and the point b4 is where line B exits FOV 522. The point b2 is determined as the start position and the point b3 is determined as the stop position for the projection for line B in order to encompass the TOF kernel for line B.

Four points are also computed for line C, including c1, c2, c3, and c4. The point c1 is where a TOF kernel starts for line C, the point c2 is where line C enters the FOV 522, the point c3 is where the TOF kernel ends for line C, and the point c4 is where line C exits the FOV 522. The point c2 is determined as the start position and the point c3 is determined as the stop position for the projection for line C in order to encompass the TOF kernel for line C.

Returning to FIG. 4, at 408, method 400 includes, for each event, computing projection coefficients (weights) based on a path length and a TOF kernel height for each voxel traversed by the TOF kernel. For example, the controller may compute a fast Siddon projection based on voxel identification and weight (e.g., derived from the path length and the TOF kernel height) in a sparse matrix multiplication. The path length and the TOF kernel height at the center of each segment may be determined for each voxel boundary crossing, for example. The controller may compute the projection for each event in the data acquired during the given time frame, for example.

Turning briefly to FIG. 6, a diagram 600 shows an illustrative example of determining the path length and the TOF kernel height for an efficient projector. Although diagram 600 shows a two-dimensional representation, note that the actual calculation may be in three dimensions. Diagram 600 shows a plurality of voxels 602, a direction vector n, which may be a portion of a LOR, for example, a start position 606, and a stop position 608. The start position 606 and the stop position 608 correspond to the start position and the stop position of the TOF kernel described above with respect to FIGS. 4 and 5 (e.g., as determined at 406). Thus, the portion of the direction vector n between the start position 606 and the stop position 608 corresponds to part of the TOF kernel that will be used in the projection of an event.

A factor $\alpha$ is defined as a distance along the direction vector n from a center of the TOF kernel. Thus, the center of the TOF kernel is at $\alpha=0$. For each step in x (e.g., dx, shown going from left to right on diagram 600), $\alpha$ changes by dx/n[0]. A "next $\alpha$" look-up may be kept for crossing voxel boundaries. A smallest step in $\alpha$ that hits a voxel boundary is used for determining path lengths and TOF kernel heights. For example, going from the start position 606 to the stop position 608 along the direction vector n, there are six voxel boundary crossings, resulting in seven segments L1, L2, L3, L4, L5, L6, and L7 of varying lengths. The length of each segment may be determined based on the change in $\alpha$. Each segment has a corresponding TOF kernel height. As shown, segment L1 has a TOF kernel height H1, segment L2 has a TOF kernel height H2, segment L3 has a TOF kernel height H3, segment L4 has a TOF kernel height H4, segment L5 has a TOF kernel height H5, segment L6 has a TOF kernel height H6, and segment L7 has a TOF kernel height H7. The length of each segment multiplied by the corresponding TOF kernel height may be stored along with the voxel ID for each voxel traversed by the direction vector n between the start position 606 and the stop position 608. A projection 610 may then be determined from a sparse matrix multiplication of the stored values.

Returning to FIG. 4, at 410, method 400 includes, for each event, performing a forward projection based on the projection coefficients (e.g., determined above at 408), applying correction(s), and backprojecting based on the projection coefficients. As an example, within each subset, each event may be forward projected, adjusted for corrections, and then backprojected. The forward and back projection may be performed by accessing the sparse matrix elements, for example, with one image reconstructed per processing thread to reduce or avoid memory locks. Further, as mentioned above with respect to 308 of FIG. 3, the reconstruction algorithm may not employ attenuation or scatter correction and may use an efficient randoms calculation.

At 412, method 400 includes combining the backprojection of each event within a given subset. For example, the backprojections from all events within the subset may be summed together, and this may be used to generate an image update. Thus, the data from each subset may provide one image update.

At 414, method 400 includes iteratively updating the image based on each subset. For example, the controller may use an iterative reconstruction algorithm that updates an image estimate until a desired solution is achieved. The desired solution may be a maximum likelihood solution, for example. As mentioned above, each subset may provide one image update. An initial blank (e.g., uniform) image may be updated using a first image update generated from a first subset of the emission data acquired during the given time frame (e.g., a first iteration). The resulting updated image may be further updated using a second image update generated from a second subset of the emission data (e.g., a second iteration). This process may be repeated with the image update from each subset of the events, enabling the image estimate to converge (e.g., reach the desired solution). The final updated image comprises the real-time PET image for one time frame. Method 400 may then return. For example, method 400 may be repeated for each subsequent time frame so that a subsequent image frame may be produced for motion detection via the method of FIG. 3.

Next, FIG. 7 shows an example implementation 700 of patient motion detection during PET based on PET image frames reconstructed in real-time. For example, a controller (e.g., controller 25 of FIG. 1 and/or controller 44 of FIG. 2) may detect the patient motion during PET acquisition according to the method of FIG. 3 using real-time PET images reconstructed using TOF list-mode reconstruction without attenuation and scatter correction, such as according to the fast reconstruction method of FIG. 4. Note that implementation 700 is one illustrative example of how the PET image frames may be analyzed to determine patient motion, and in other examples, the controller may perform other analyses.

Implementation 700 shows a series of PET image frames reconstructed from emission data acquired over time, including a first image frame 702, a second image frame 704, and a third image frame 706. Each of the first image frame 702, the second image frame 704, and the third image frame 706 are reconstructed from data acquired over a short duration (e.g., 1 second each), as described above with respect to FIGS. 3 and 4, and each show a side profile of a patient's skull. The first image frame 702 is the earliest frame, and the third image frame 706 is the latest time frame, as shown by a time axis 701. In particular, the first image frame 702 is the first image frame in the series (e.g., frame 1), and the second image frame 704 is the next image frame in the series (e.g., frame 2, immediately following frame 1 without any other image frames in between). The third image frame 706 is some number of image frames following the second image frame 704 (e.g., frame n).

In the example implementation 700, upon reconstructing each image frame, the controller performs registration to transform the image frame onto a unified coordinate system, shown as a grid, and uses edge detection to define boundaries of the patient's anatomy in each image frame. FIG. 7 shows a first boundary line 708 for the top of the patient's skull in the first image frame 702, a second boundary line 710 for the top of the patient's skull in the second image frame 704, and a third boundary line 712 for the top of the patient's skull in the third image frame 706, although other boundary lines additionally or alternatively may be used for determining and tracking patient motion between image frames. Further, for comparison, the first boundary line 708 is shown as a dashed overlay on the second image frame 704, and both the first boundary line 708 and the second boundary line 710 are shown as dashed overlays on the third image frame 706.

Once at least two image frames are acquired (e.g., the first image frame 702 and the second image frame 704 in the example shown in FIG. 7), the controller compares positions of corresponding boundary lines between the two image frames to determine a displacement between them. In the example shown, the patient's skull has shifted between the first image frame 702 and the second image frame 704, as illustrated by the position of the second boundary line 710 relative to the first boundary line 708 on the second image frame 704. The controller may directly determine a magnitude of the displacement based on the difference in the position of the second boundary line 710 relative to the first boundary line 708 and indicate patient motion responsive to the magnitude exceeding a threshold, as described above at 312 of FIG. 3.

In some examples, the boundaries of non-consecutive image frames in the series may also be compared to track patient motion over time. In the example shown, the third boundary line 712 is compared to both the second boundary line 710 and the first boundary line 708 even though one or more image frames are acquired between the second image frame 704 and the third image frame 706. The position of the third boundary line 712 relative to the second boundary line 710 shows that the patient's skull has shifted between the second image frame 704 and the third image frame 706 in the same direction as between the first image frame 702 and the second image frame 704 (e.g., in the downward direction with respect to the page), although it may be understood that image frames following the second image frame 704 and preceding the third image frame 706 may show patient motion in other directions. For example, the patient may move in the upward direction (with respect to the page) before moving downward again and reaching the position shown in the third image frame 706.

The controller may determine a displacement between the third boundary line 712 and one or both of the first boundary line 708 and the second boundary line 710. The magnitude of the displacement between the third boundary line 712 and the second boundary line 710 is smaller than the magnitude of the displacement between the first boundary line 708 and the second boundary line 710. Further, the displacement between the first boundary line 708 and the third boundary line 712 is the greatest. As one example, the series shown in example implementation may indicate that the patient is consistently moving in the downward direction depending on any displacement shown in intervening image frames between the second image frame 704 and the third image frame 706. In some examples, the controller may generate a plot of the displacement (or change in boundary position) between consecutive image frames to track the patient motion over time in both magnitude and direction. Further, in some examples, the plot may be displayed to an operator in real-time (e.g., at 324 of FIG. 3).

Figure 8:
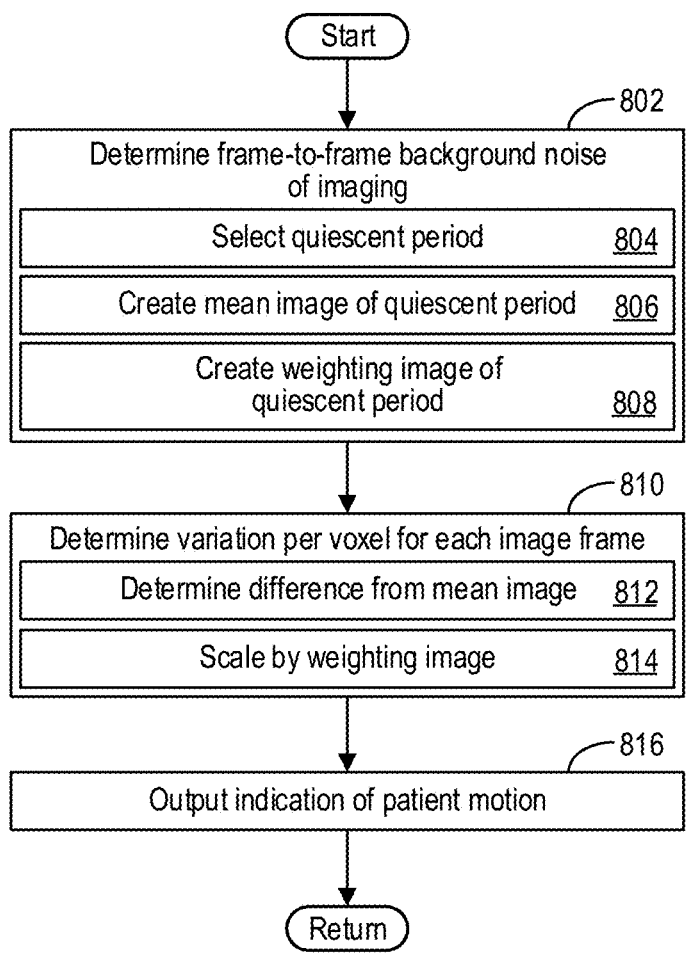
FIG. 8 shows a flow chart of a first exemplary method for detecting patient motion based on a variation per voxel that uses a fixed reference to detect voxel-wise variation.

Next, FIG. 8 shows a first example method 800 for detecting patient motion on a per-voxel basis and without image registration, as introduced with respect to FIG. 3. For example, method 800 may be performed by a controller as a part of method 300 of FIG. 3 (e.g., at 310) in real-time during PET data acquisition (e.g., PET imaging) by an imaging system. At least parts of method 800 may be performed for a single image frame and may be repeated for each additional image frame in real-time, at least in some examples.

At 802, method 800 includes determining a frame-to-frame background noise of the imaging. The frame-to-frame background noise may correspond to variances in a signal between each image frame that are not due to patient motion. For example, because a finite number of annihilation photons is detected during a given time period, there will be statistical fluctuations in the number of events along a particular line of response, and these fluctuations result in fluctuations in the reconstructed image.

Determining the frame-to-frame background noise of the imaging comprises selecting a quiescent period, as indicated at 804. The quiescent period may comprise a pre-determined duration during the imaging and may occur during an initial portion of the imaging (e.g., within the first minute of the imaging or the first several minutes of the imaging). For example, the pre-determined duration may be between 5 and 15 seconds. As one non-limiting example, the pre-determined duration may be 10 seconds. The patient may be inactive during the quiescent period, and thus, patient motion is not expected. As one example, an operator of the imaging system may manually select the quiescent period, such as by analyzing recently acquired frames for patient movement. As another example, the controller may select the quiescent period by evaluating the image frames for motion on a pre-determined time delay. In some embodiments, the controller may use image registration to check for patient motion throughout the duration. Then, after the quiescent period is selected, image registration may not be used to detect subsequent patient motion.

In some examples, events detected during the selected quiescent period may be divided into N interleaved subsets, where data for each subset is distributed over the entire pre-determined duration. For example, if N is equal to 10, events 1, 11, 21, etc. may be used to generate a first image of the quiescent period; events 2, 12, 22, etc. may be used to generate a second image of the quiescent period; and so forth. As a result, N independent images may be generated that correspond to a same motion state, with any difference between the images caused by the statistical fluctuations described above at 802 (and not due to patient motion between the images) because all of the images include data spanning the entire pre-determined duration.

Determining the frame-to-frame background noise of the imaging further comprises creating a mean image of the quiescent period, as indicated at 806. The mean image may be generated by calculating a mean value for each voxel. For example, a value of a given voxel in one frame (which directly relates to signal strength output by a corresponding detector crystal) may be summed with the value of that same voxel in every other frame and then divided by a total number of frames in the selected quiescent period to generate the mean value for that voxel in the mean image.

Determining the frame-to-frame background noise of the imaging further comprises creating a weighting image of the quiescent image, as indicated at 808. The weighting image is used to weight the deviation from the mean intensity according to an amount of fluctuation that is expected to occur at each voxel. As one example, the weighting image may be a standard deviation image that is generated by calculating a separate standard deviation for each voxel based on the individual intensities of the given voxel in each frame in the selected quiescent period, the mean of the given voxel (e.g., as determined at 806), and the total number of frames in the selected quiescent period, such as by using a known formula for calculating the standard deviation. However, the standard deviation is one example of a quantity that may be used to give a measurement of variance for the weighting image, and other methods may be used to estimate the weight to be given to a deviation from the mean intensity. For example, the largest and smallest value observed for a particular voxel during the quiescent period may be used to determine the measurement of variance (e.g., the deviation from the mean intensity). Thus, any approach that enables the controller to identify an expected variation from frame to frame may be used to generate the weighting image. Together, the mean image and the weighting image may provide a background noise reference that is used to remove the background noise from each voxel for each image frame in order to obtain variation that is due to patient motion, as will be elaborated below.

At 810, method 800 includes determining a variation per voxel for each image frame. Determining the variation per voxel for each image frame comprises determining a difference from the mean image, as indicated at 812. For each image frame, the controller may subtract the mean value of a given voxel from the value of the corresponding voxel in the current image frame to determine the difference from the mean image. Thus, a difference may be determined for each individual voxel in each individual image frame.

Determining the variation per voxel for each image frame further comprises scaling by the weighting image, as indicated at 814. When the standard deviation is used for the weighting, the difference for a given voxel may be scaled by the standard deviation determined for that same voxel. For example, the difference may be divided by the standard deviation to scale by the standard deviation image. However, other measurements of variance may be used to scale the observed deviation from the mean image, such as mentioned above at 808, in order to identify voxels that have a larger than expected variation. The output comprises the variation, which may be a value (or metric) corresponding to a magnitude of the variation at that voxel. For example, the value may increase as the magnitude of the variation at that voxel increases.

At 816, method 800 includes outputting an indication of patient motion. As one example, the indication of patient motion may be output as a map of z-scores, which may be referred to herein as a z-map. A z-score refers to the number of standard deviations of the determined variation of a given voxel from the corresponding voxel in the mean image. Thus, a z-score of zero indicates the voxel value is equal to the mean, and no patient motion is detected at that voxel. Further, as the z-score increases, the variation at the given voxel, and the probability that motion is detected at that voxel, increases. Thus, the z-score may provide a magnitude of voxel-wise variation and detected motion at each voxel. The z-map may be colorized such that the color of each voxel (or pixel of a 2D image representing the 3D volume) indicates the magnitude of the z-score, such as illustrated in FIG. 13 and described below. For example, a z-score greater than 3 indicates that the variation of the voxel is greater than three standard deviations from the mean.

As another example, the indication of patient motion may be output as an overlay that selectively colorizes voxels having a determined variation that is greater than a threshold variation. The threshold variation may be a pre-determined non-zero value that is stored in the memory of the controller and may be used to differentiate variation that occurs due to, for example, shallow breathing and cardiac motion from variation that occurs due to deep breaths, the patient changing their pose, etc. As another example, the threshold variation may be calculated. For example, the controller may determine the threshold variation as a multiple (t) of the standard deviation. For example, to identify all voxels having a variation greater than three standard deviations, t may be set to 3. Further, because the deviation may be positive or negative, the absolute value may be used. As still another example, an intensity of the colorization may scale according to an intensity of the determined variation of the corresponding voxel, with darkly colored voxels corresponding to higher variation absolute values, lightly colored voxels corresponding to lower variation absolute values, and uncolored voxels corresponding to voxels with substantially no variation from the background noise.

Thus, the colorized portions may distinguish portions of the image frame that have detected patient motion (e.g., voxels where the determined variation is greater than the threshold variation) from portions of the image frame that do not have detected patient motion (e.g., voxels where the determined variation is not greater than the threshold variation). An example of the colorized overlay is illustrated with respect to FIG. 14 and will be described below.

As yet another example, the indication of patient motion may be output as a motion plot that is generated from the per-voxel variation. For example, the motion plot may be displayed as a function of frame number or time (e.g., in seconds). As one example, the controller may count the number of voxels having variations over the threshold variation in a binary fashion, wherein a first voxel having a determined variation that is greater than the threshold variation is counted and a second voxel having a determined variation that is not greater than the threshold is not counted. In such an example, the motion plot may show the number of voxels having variations over the threshold variation for each frame. As another example, a transfer function may be used to differently weight voxels based on the absolute value of the determined variation. For example, smaller absolute values may be given relatively less weight than larger absolute values. In such an example, the motion plot may show a sum of the transformation for each frame.

Figure 15:
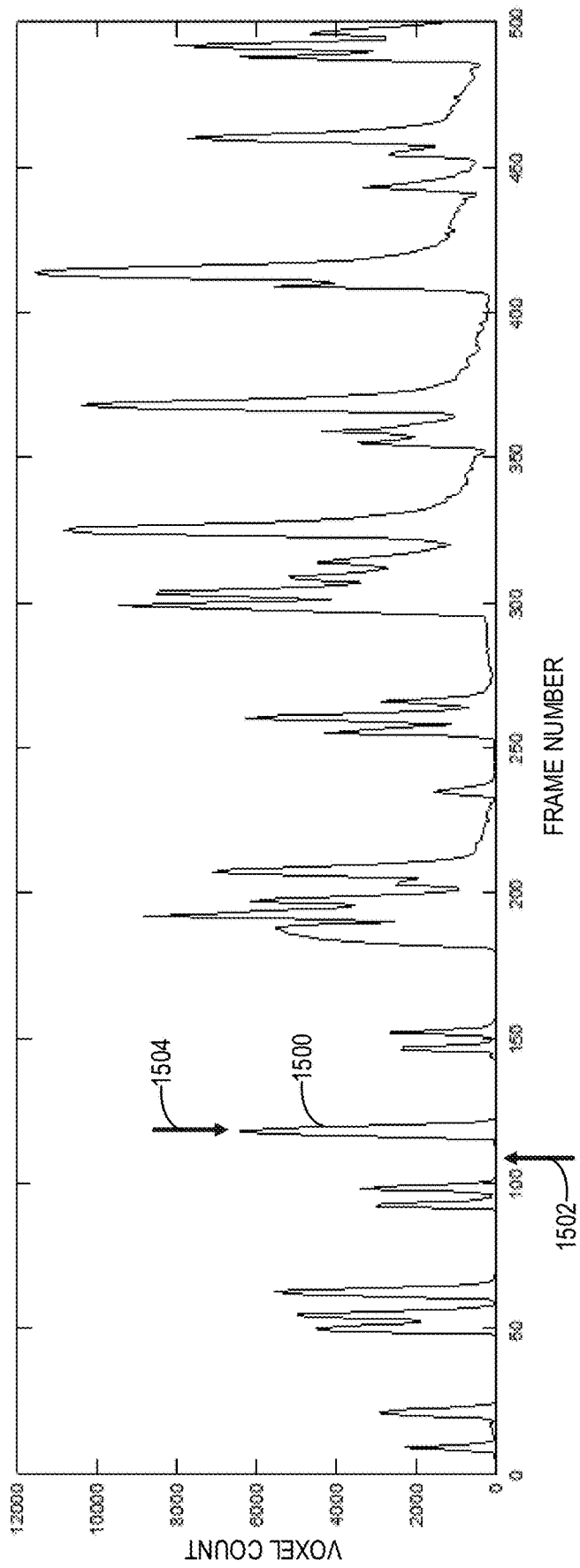
FIG. 15 shows an example of indicating patient motion by counting voxels over a motion threshold.

As another example, the controller may determine a standard deviation of the variation across all voxel and all time, which may be defined as σ. The number of voxels over the threshold variation (n) may be calculated as:

$$n=\Sigma(|v_i-m_i|>t\cdot\sigma_i)$$

where $v_i$ is a voxel in the imaged volume, $m_i$ is the mean value of that voxel, t is a threshold value, e.g. 3, and $\sigma_i$ is the standard deviation of the voxel. An example of the motion plot is illustrated in FIG. 15 and will be described below. Further, it may be understood that any or all of the z-map, the colorized overlay, and the motion plot may be used to indicate patient motion. Method 800 may then return. For example, at least portions of the method may be repeated for each image frame during the PET imaging (e.g., from 810-816).

Figure 9:
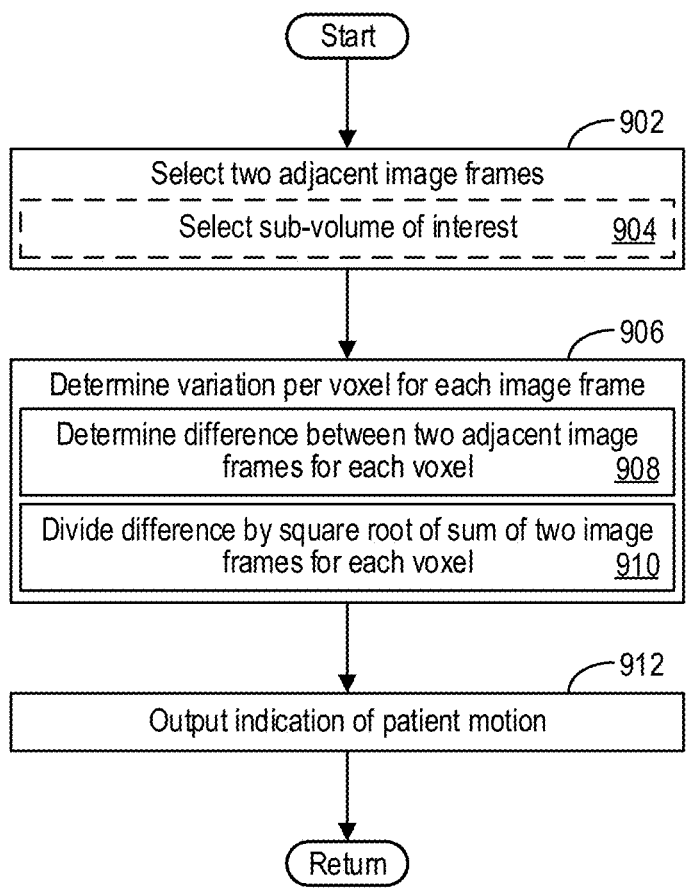
FIG. 9 shows a flow chart of a second exemplary method for detecting patient motion based on a variation per voxel that uses adjacent image frames to detect voxel-wise variation.

Turning now to FIG. 9, a second example method 900 for detecting patient motion on a per-voxel basis and without image registration is shown. For example, method 900 may be performed by a controller as a part of method 300 of FIG. 3 (e.g., at 310) in real-time during PET data acquisition (e.g., PET imaging) by an imaging system. At least parts of method 900 may be performed for a single image frame and may be repeated for each additional image frame in real-time, at least in some examples.

At 902, method 900 includes selecting two adjacent image frames. "Adjacent image frames" may refer to image frames that are sequential in time and frame number, with no other image frames therebetween. For example, the controller may select a most recently generated live PET image (e.g., image frame i) and the immediately preceding live PET image (e.g., image frame i–1). In some examples, selecting the two adjacent image frames may include selecting a sub-volume of interest, as optionally indicated at 904. For example, the sub-volume of interest ($S_i$) may be selected manually by an operator of the imaging system (e.g., using a 3D viewer or another program). The sub-volume of interest may be equal to a full volume of the live PET image ($V_i$) or may focus on a region of highest radionuclide uptake or greatest variation. In other examples, the sub-volume of interest may be automatically selected by the controller according to pre-programmed instructions. For example, the controller may use a machine learning algorithm that detects which region of the volume has the highest value (e.g., corresponding to the highest radionuclide uptake) and/or greatest variation and set the sub-volume accordingly. As a further example, the sub-volume of interest may be selected based on voxel intensity, wherein only regions containing voxels with the highest intensity are selected. For example, only 5% of voxels with the highest intensity may be included. A region that is defined by voxel intensity may be further modified by using erosion and dilation operations in order to remove isolated voxels from the area of interest while including the immediate vicinity of regions of contiguous high intensity voxels in order to permit observation of motion. Further, the regions included in the sub-volume of interest may not be contiguous with each other. For example, the sub-volume of interest may include a first region of contiguous voxels and a second region of contiguous voxels that is spaced apart from, and not adjoining, the first region. Although two regions are given in the above example, it may be understood that the sub-volume of interest may include any number of regions.

At 906, the method includes determining a variation per voxel for each image frame (or for the selected sub-region of interest within the image frame). The variation per voxel may be referred to as a variation metric ($M_i$). The variation metric is separately calculated for each voxel (or pixel of a 2D image representing the 3D volume) for each image frame. In this example, the variation per voxel measures an amount of change at the given voxel between the adjacent image frames. Thus, the immediately preceding live PET image frame i–1 may be used as a reference for the current live PET image frame i.

Determining the variation per voxel for each image frame includes determining a difference between the two adjacent image frames for each voxel, as indicated at 908. For example, a value of a given voxel in image frame i–1 may be subtracted from the value of that same voxel in image frame i to determine the difference between the two adjacent image frames.

Determining the variation per voxel for each image frame further includes dividing the difference by a square root sum of the two image frames for each voxel. Dividing the difference by the square root sum of the two images may serve as a proxy for standard deviation. For example, the square root sum of the two image frames may be calculated by summing the measured value for the given voxel in image frame i and image frame i–1 and taking the square root of this value. The difference (e.g., as defined at 908) may be divided by the resulting square root sum. Note that although the difference and the square root sum are described separately, the variation per voxel may be determined using a single equation that takes into account both parameters.

At 912, method 900 includes outputting an indication of patient motion, such as described above at 816 of FIG. 8. For example, the indication of patient motion may be output by showing areas of motion on the image frame (e.g., via an overlay or a z-map) and/or via a motion plot.

Method 900 then returns. For example, method 900 may be repeated for each image frame. In particular, method 900 may be used to detect high-frequency motion, as comparing two adjacent image frames may not be sensitive to slow drift that may not be readily apparent from image frame to image frame.

Figure 10:
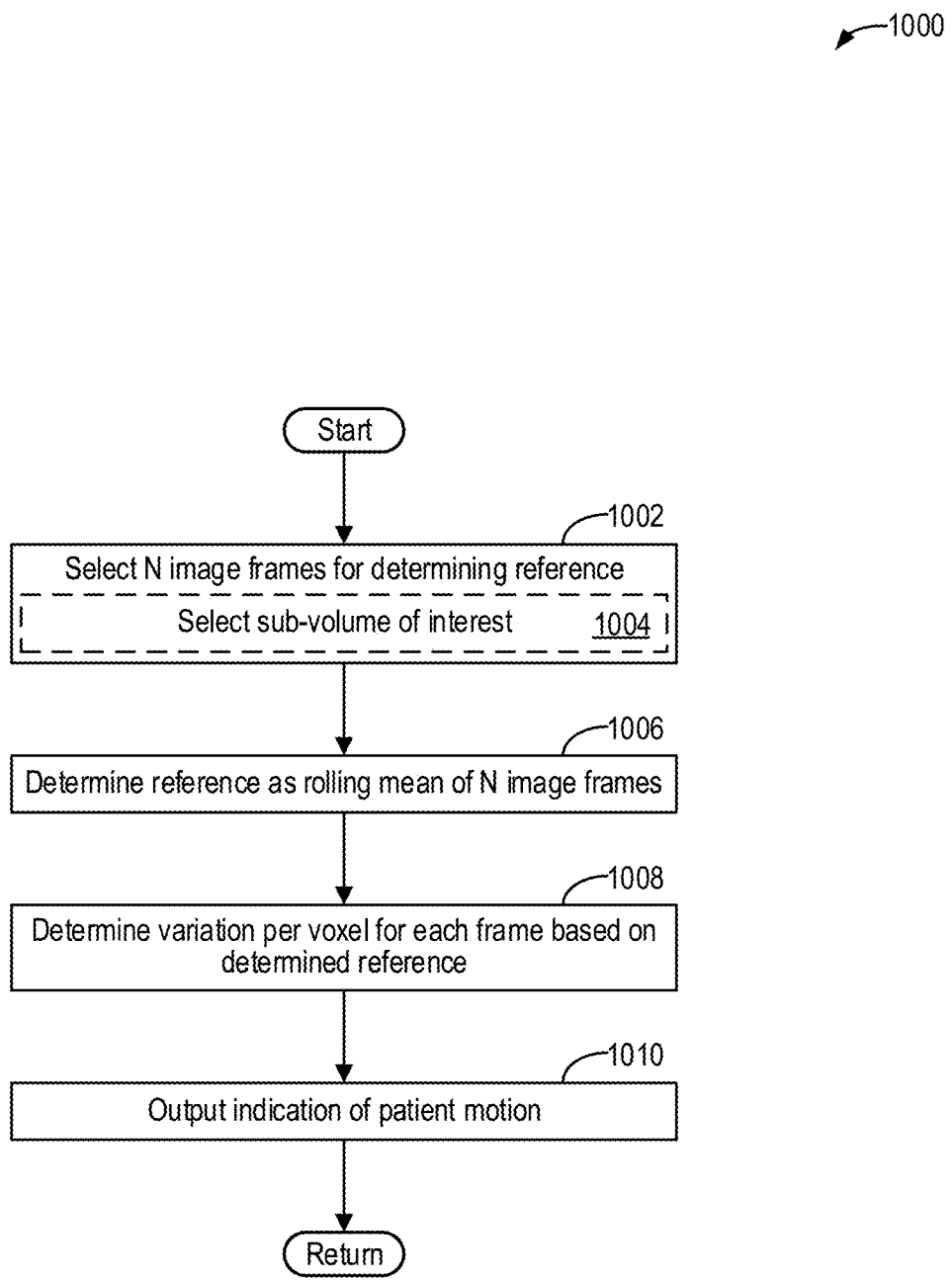
FIG. 10 shows a flow chart of a third exemplary method for detecting patient motion based on a variation per voxel that uses a rolling mean reference to detect voxel-wise variation.

Continuing to FIG. 10, a third example method 1000 for detecting patient motion on a per-voxel basis and without image registration is shown. For example, method 1000 may be performed by a controller as a part of method 300 of FIG. 3 (e.g., at 310) in real-time during PET data acquisition (e.g., PET imaging) by an imaging system. At least parts of method 1000 may be performed for a single image frame and may be repeated for each additional image frame in real-time, at least in some examples.

At 1002, method 1000 includes selecting N image frames for determining a reference. "N" refers to a non-zero, integer number of consecutive image frames. For example, N may be a pre-programmed number stored in a memory of the controller. As one example, N may be greater than two. As another example, the N frames may be acquired over a pre-determined duration (e.g., 10 seconds). Selecting the N image frames may include selecting the N previous frames from a current live PET image. In other examples, selecting the N image frames may include selecting the N/2 image frames immediately preceding the current live PET image and the N/2 image frames obtained immediately after the current live PET image. In some examples, selecting the two adjacent image frames may include selecting a sub-volume of interest, as optionally indicated at 1004, such as described above at 904 of FIG. 9. Further, the reference may comprise a background noise reference that is used to remove background-related variation in order to determine changes in each voxel due to patient motion, such as described above with respect to FIG. 8 and elaborated below.

At 1006, method 1000 includes determining the reference as a rolling mean of the N image frames (or selected sub-volume within the N image frames). The rolling mean is updated as new data is acquired and is different than the mean image described with respect to FIG. 8. For example, the mean image generated at 806 of FIG. 8 is a static mean image based on a single quiescent period and does not change throughout the imaging, whereas the rolling mean is updated as each new image frame is acquired. As one example, the reference image may be calculated as a boxcar average of the N previous image frames (e.g., when the selected N image frames include the N previous image frames). In other examples, the reference image may be calculated as an exponential average of the selected N image frames or as a time-weighted average of the selected N image frames. As still another example, the reference image may be calculated as a local average of the selected N image frames, such as when the selected N image frames include N/2 image frames before and N/2 image frames after the current image frame. In some examples, interleaved subsets may be used for generating the rolling mean, such as described above with respect to the quiescent period of FIG. 8. Thus, a rolling mean value for each voxel may be generated for the reference that is equally weighted, time-weighted, or exponentially weighted.

As one non-limiting example, the reference ($R_i$) may be calculated for each voxel of the selected sub-volume $S_i$ using the following equation:

$$R_i = \sum_{j=1}^{j=N} \frac{w_j S_{i-j}}{N-1}$$

where $w_j=1\forall j$ or $w_j=e^{-j/\alpha N}$ and $\alpha$ represents a damping factor (e.g., $\alpha=3$).

At 1008, method 1000 includes determining a variation per voxel for each frame based on the determined reference. For example, the variation per voxel may be a variation metric $M_i$ as introduced above with respect to FIG. 9. The variation may be calculated by subtracting the reference for a given voxel from the value for the current image frame and scaling by the reference. As one example, the variation may be calculated using the following equation:

$$M_i = \frac{\Sigma S_i - R_i}{\Sigma R_i}$$

where the resulting $M_i$ value is for one voxel of the selected sub-volume of each image frame.

At 1010, method 1000 includes outputting an indication of patient motion. For example, the indication of patient motion may be output by showing areas of motion on the image frame (e.g., via an overlay or a z-map) and/or via a motion plot, such as described above at 816 of FIG. 8. As explained above, the variation metric may be compared to a threshold variation, and voxels having variation over the threshold variation may be colorized via the overlay and/or counted and displayed as the motion plot.

Method 1000 then returns. For example, method 1000 may be repeated for each image frame. In particular, method 1000 may be better at detecting lower frequency motion, such as slow drift, than method 900 of FIG. 9 due to the reference being comprised of multiple images.

Figure 11:
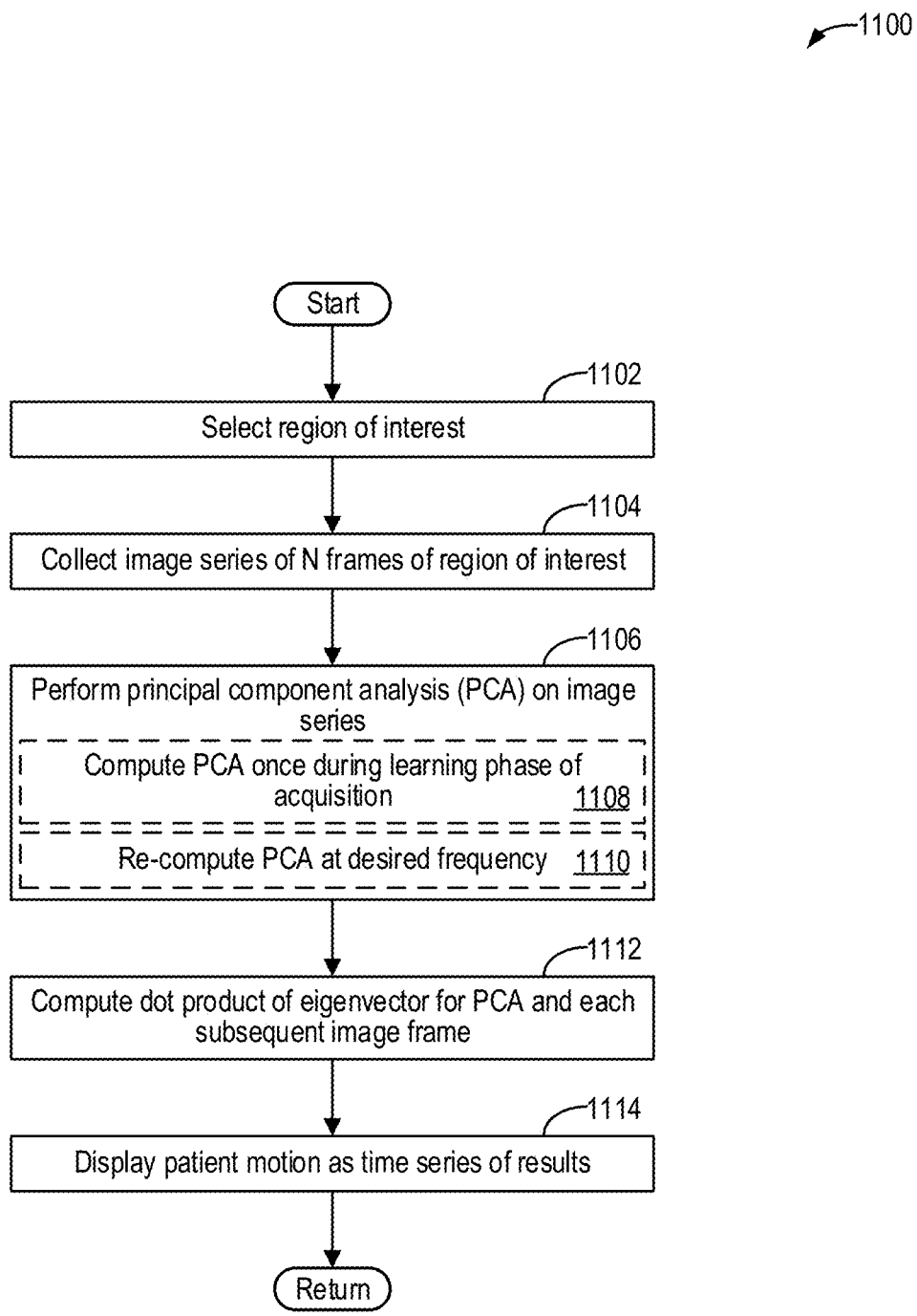
FIG. 11 shows a flow chart of a fourth exemplary method for detecting patient motion based on a variation per voxel that uses principal component analysis (PCA) to detect voxel-wise variation.

Next, FIG. 11 shows a fourth example method 1100 for detecting patient motion on a per-voxel basis and without image registration is shown. For example, method 1100 may be performed by a controller as a part of method 300 of FIG. 3 (e.g., at 310) in real-time during PET data acquisition (e.g., PET imaging) by an imaging system. At least parts of method 1100 may be performed for a single image frame and may be repeated for each additional image frame in real-time, at least in some examples.

At 1102, method 1100 includes selecting a region of interest. The region of interest may be a sub-volume of interest of a total volume imaged, for example, as described above with respect to FIG. 9 (e.g., at 904).

At 1104, method 1100 includes collecting an image series of N frames of the region of interest. As described above with respect to FIG. 10, "N" refers to a non-zero, integer number of consecutive image frames. For example, N may be a pre-programmed number stored in a memory of the controller that is greater than two. As one non-limiting example, N may be 40 consecutive image frames. As another example, the N frames may be acquired over a pre-determined duration (e.g., 10 seconds).

At 1106, method 1100 includes performing a principal component analysis (PCA) on the image series. The PCA may identify dominant components as eigenvectors from a covariance matrix based on a sorted subset of the acquired PET data from the image series. In particular, the PCA may identify variations in time that are due to cyclic (e.g., periodic) motion, such as respiratory motion and cardiac motion. Further, the controller may perform a frequency analysis of the several most dominant components identified by the PCA in order to determine a strongest component for a frequency of interest (e.g., around 1 Hertz, or Hz, for cardiac motion and around 0.25 Hz for respiratory motion). The frequency analysis may include performing a fast Fourier transform (FFT), for example. An example of the frequency analysis is illustrated with respect to FIG. 19 and described below.

As one example, the method includes computing the PCA once during a learning phase of the acquisition, as optionally indicated at 1108. The learning phase of the acquisition may occur during a beginning of the PET data acquisition, for example, such as within an initial minute of the PET data acquisition. As another example, the method includes re-computing the PCA at a desired frequency, as optionally indicated at 1110. For example, the PCA may be re-computed after a desired amount of time has passed, such as a number of seconds (e.g., 10 seconds) or minutes (e.g., 1 minute).

At 1112, method 1100 includes computing a dot product of an eigenvector for the PCA and each subsequent image frame. For example, the PCA may be applied to a subset of voxels that are most likely to contain information about cardiac or respiratory motion (e.g., the heart and its surrounding voxels). When a time series (N frames) of M such voxels is transformed into a matrix of M×N, the principal component analysis may generate a new matrix U (with M×N elements) that describes how motion in the image translates into changes in intensity in the image. The dot product of a column of U (corresponding to one of the principal components) with each column of the M×N matrix produces a set of values that can be interpreted as a time series that shows how the image is moving in time (where a high value corresponds to motion in a first direction and a low value corresponds to motion in a second, opposite direction). In most instances, one of the first few principal components (first columns of U) will contain the information representing either the cardiac or respiratory waveforms. This waveform can be directly displayed and may give a real-time indication of patient respiratory or cardiac motion.

At 1114, method 1100 includes displaying patient motion as a time series of results. For example, the results may be output as a cardiac trace for a cardiac frequency of interest and a respiratory trace for a respiratory frequency of interest, as illustrated in FIG. 20 and described below. The time series of results may show how the signal at the given frequency changes over time, for example.

Method 1100 then returns. For example, at least portions of method 1100 may be repeated for each image frame. For example, 1112-1114 may be repeated for each image frame, or 1110-1114 may be repeated for each image frame.

Figure 12:
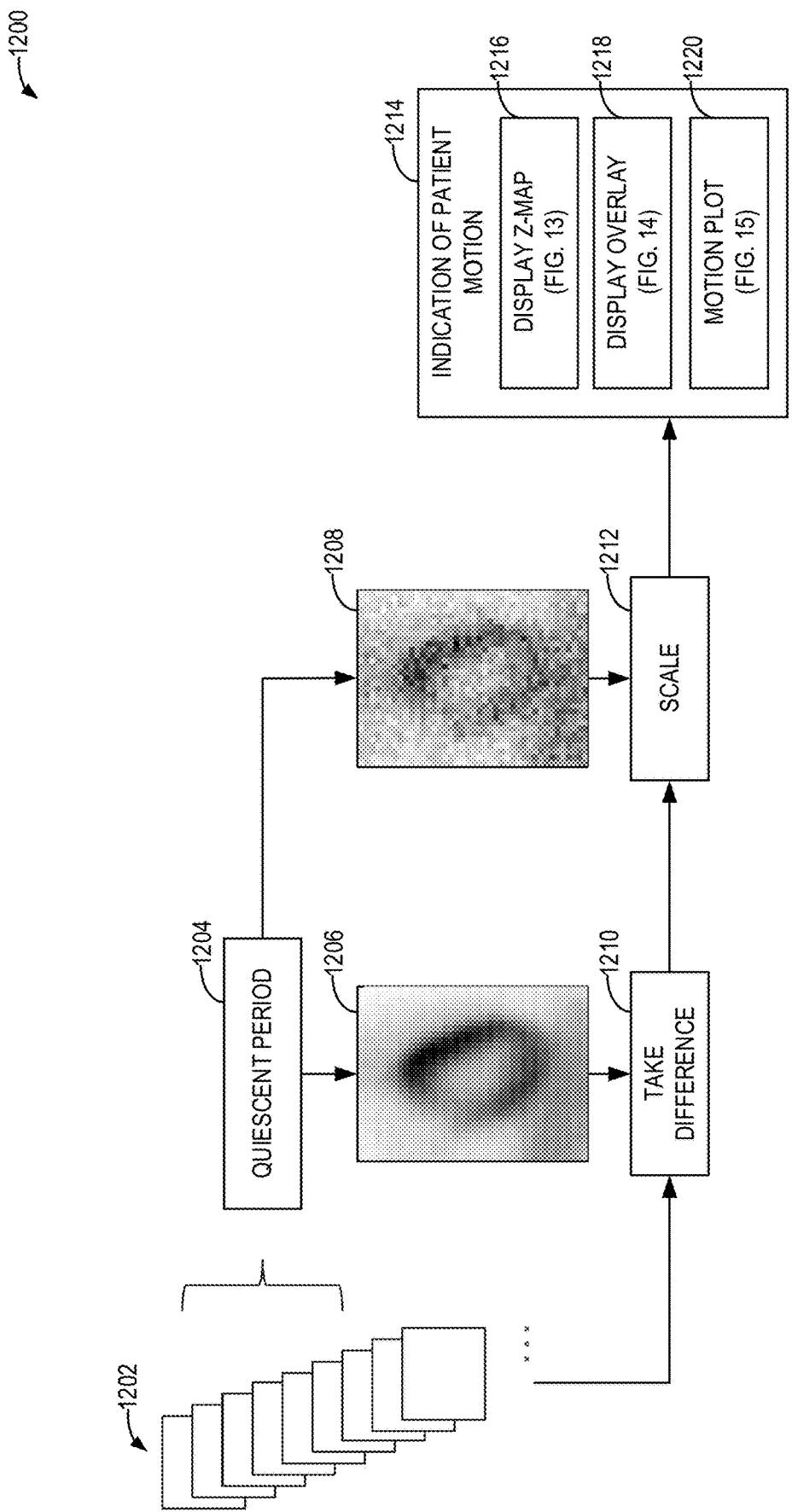
FIG. 12 schematically shows a block diagram of an algorithm for determining patient motion in live PET images by comparing each voxel to a mean image and a standard deviation image from a reference period.

Turning now to FIG. 12, a block diagram of an algorithm 1200 for detecting patient motion in live PET images in a voxel-wise fashion is shown. For example, the algorithm 1200 may correspond to the method 800 of FIG. 8. A series of live PET images 1202 is acquired, and a quiescent period 1204 is selected from a subset of the series of live PET images 1202 and used to generate a mean image 1206 and a standard deviation image 1208. To determine a variation for each voxel, the mean image 1206 is compared to a current image frame of the series of live PET images 1202, and a difference 1210 is obtained for each voxel. The difference 1210 is scaled 1212 by the standard deviation image 1208 for each voxel. The corresponding output is used to provide an indication of patient motion 1214, which may be displayed as a z-map 1216, an overlay 1218, and/or a motion plot 1220 of voxels having the variation over a threshold variation. An example of the z-map 1216 is shown in FIG. 13, an example of the overlay 1218 is shown in FIG. 14, and an example of the motion plot 1220 is shown in FIG. 15.

Turning now to FIG. 13, a first motion color map 1300 of a first image frame and a second motion color map 1302 of a second image frame are shown. The first motion color map 1300 includes a first z-map 1304 that depicts a z-score for each voxel of the first image frame and a color scale bar 1306. The second motion color map 1302 includes a second z-map 1308 that depicts a z-score for each voxel of the second image frame and the color scale bar 1306. The color scale bar 1306 relates the color of each z-score, which is positioned according to the position of the corresponding voxel in the image frame, to a magnitude of the z-score, with dark red denoting a highest z-score (e.g., 6) and dark blue denoting a lowest z-score.

Patient motion is not detected in the first image frame, as indicated by the blue and cyan coloring of every z-score of the first z-map 1304. In contrast, patient motion is detected in the second image frame, as indicated by the yellow to dark red portions of the second z-map 1308. In particular, the second z-map 1308 indicates regions of the second image frame experiencing the greatest variation, and thus those regions of the image most affected by patient motion, in dark red.

Continuing to FIG. 14, an example of outputting patient motion as a colorized overlay on an image is shown. A first image frame 1400, which may correspond to the z-map 1304 of FIG. 13, does not have any colorized portions, indicating that no patient motion is detected. In contrast, select voxels (represented as pixels of a 2D image) are colorized in a second image frame 1402, where patient motion is detected. The second image frame 1402 may correspond to the second z-map 1308 of FIG. 13. In the example shown, the colorized voxels are red, although other colors or methods of distinguishing the voxels experiencing variation from those that are not experiencing variation may be used (e.g., highlighting, outlining, etc.). Further, an intensity of the red color corresponds to a magnitude of the variation at each voxel, with lighter coloration corresponding to voxels having less variation and darker coloration corresponding to voxels having greater variation. As such, the colorized overlay provides an indication of the regions of the image frame where patient motion is detected as well as the magnitude of the patient motion.

Next, FIG. 15 shows an exemplary motion plot 1500 that relates a voxel count of voxels having a determined variation over a threshold variation ("voxel count," as labeled on the vertical axis) to a frame number of an image frame ("frame number," as labeled on the horizontal axis). An arrow 1502 indicates a first image frame where patient motion is not detected, and an arrow 1504 indicates a second image frame where patient motion is detected. For example, the first image frame may be the same as the first image frame 1400 of FIG. 14 and having the first z-map 1304 of FIG. 13, and the second image frame may be the same as the second image frame 1402 of FIG. 14 and having the second z-map 1308 of FIG. 13.

In general, as the plotted voxel count increases for a given frame, the greater the detected patient motion is for that frame. As can be seen in the motion plot 1500, the first image frame indicated by the arrow 1502 does not include any voxels with variations over the threshold variation, whereas the second image frame indicated by the arrow 1504 includes a relatively large number of voxels (e.g., around 6000 voxels) having variations greater than the threshold variation. As such, an operator may use the motion plot 1500 to observe how the overall patient motion changes over time as each frame is acquired.

However, appropriately setting a value of the threshold variation affects the voxel count, as setting the threshold variation too low may result in motion being difficult to distinguish from noise and setting the threshold variation too high may result in patient motion being overlooked.

Figure 16:
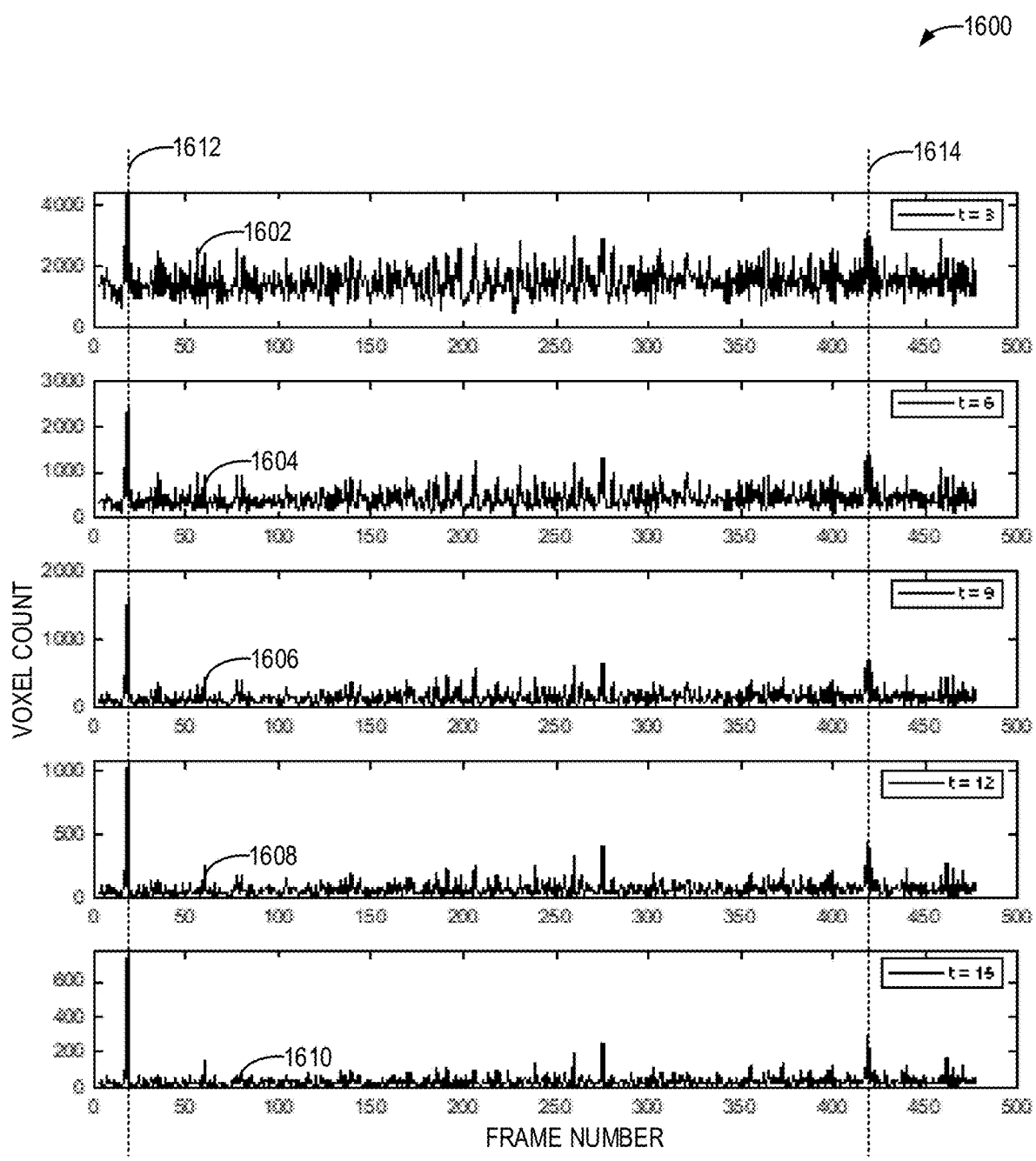
FIG. 16 shows example plots of a patient motion metric for a plurality of different motion thresholds.

Thus, FIG. 16 shows a set of motion plots 1600 where different values are used for the threshold variation. The set of motion plots 1600 are similar to the motion plot 1500 of FIG. 15 and each include the voxel count as the vertical axis and the frame number as the horizontal axis. Further, each plot in the set of motion plots 1600 is aligned with respect to the frame number. As described above with respect to FIG. 8, the threshold variation may be determined as a multiple (t) of the standard deviation. The set of motion plots 1600 includes a first plot 1602 having a threshold variation where t is 3, a second plot 1604 having a threshold variation where t is 6, a third plot 1606 having a threshold variation where t is 9, a fourth plot 1608 having a threshold variation where t is 12, and a fifth plot 1610 having a threshold variation where t is 16. Thus, the fifth plot 1610 has the threshold variation with the highest value.

To illustrate the effect of the different values of the threshold variation, two motion events are highlighted on the set of motion plots 1600 by dashed lines: a first motion event 1612 and a second motion event 1614. The first motion event 1612 corresponds to a larger patient motion than the second motion event 1614 but may still correspond to a relatively subtle motion event, such as the patient taking a deeper-than-average breath. It may be understood that additional motion events are also shown but not highlighted. The first plot 1602 includes a greatest amount of noise, but the first motion event 1612 is still viewable as a spike in the voxel count. However, the spike in the voxel count becomes more apparent as the value of the threshold variation increases, with the clearest distinction in the fifth plot 1610. The second motion event 1614 is not readily apparent in the first plot 1602 and is somewhat difficult to distinguish in the second plot 1604. However, although the threshold variation value is the highest for the fifth plot 1610, the second motion event 1614 is still distinguishable as a small spike in the signal of the fifth plot 1610. As such, determining the per-voxel variation and counting the number of voxels over the threshold variation may provide sensitive detection of patient motion when the threshold variation is appropriately set.

Figure 17:
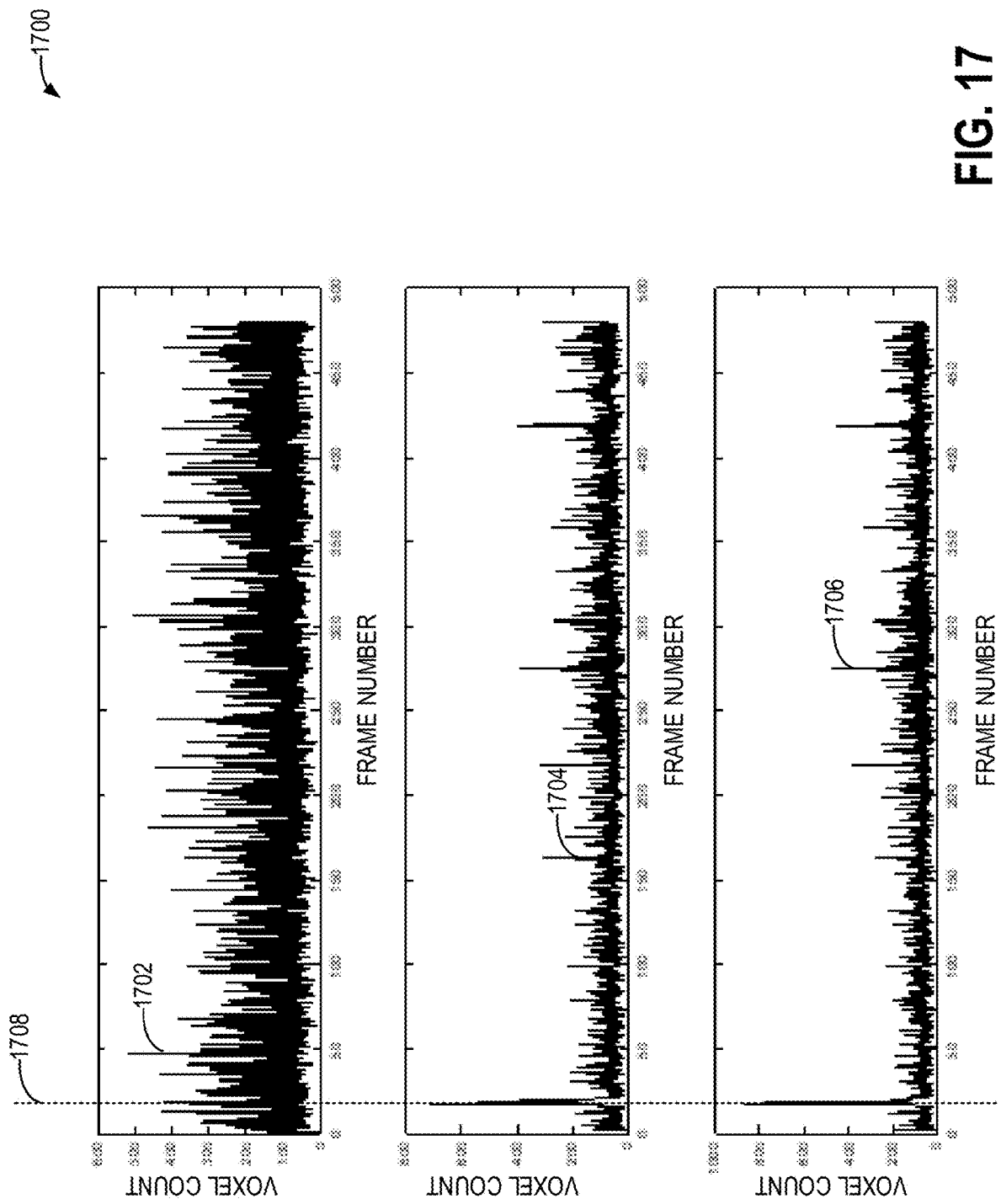
FIG. 17 shows a set of plots comparing patient motion tracking for a plurality of different voxel-wise methods over a first, longer duration.

Further, different methods of determining the per-voxel variation may result in increased accuracy in determining patient motion relative to others. Turning now to FIG. 17, a set of motion plots 1700 is shown, where each plot corresponds to a different method of determining the per-voxel variation. The set of motion plots 1700 are similar to the motion plot 1500 of FIG. 15 and each include the voxel count as the vertical axis and the frame number as the horizontal axis. The set of motion plots 1700 includes a first plot 1702 where the per-voxel variation is determined using a first method, a second plot 1704 where the per-voxel variation is determined using a second method, and a third plot 1706 where the per-voxel variation is determined using a third method.

To illustrate the effect of the different methods for calculating the per-voxel variation, an example motion event 1708 is highlighted on the set of motion plots 1700 by a dashed line (although it may be understood that other motion events are also present). In the present example, the motion event 1708 is a deep breath. As shown in the first plot 1702, the first method is very sensitive to frame-to frame motion and shows a rapidly changing signal due to the beating heart being in the field of view. For example, the first method may use adjacent image frames to approximate a mean (e.g., as described with respect to FIG. 9). The motion event 1708 is not distinguishable from the rapidly changing signal. As such, the first method may be more useful for detecting cardiac motion, but may not be useful for detecting slower (e.g. respiratory) motion. In contrast, the second plot 1704 and the third plot 1706 clearly show the motion event 1708 as a spike in the voxel count, as the second method and the third method are less sensitive to cardiac motion. For example, the second method may use a boxcar average of a number of preceding image frames in determining the per-voxel variation, and the third method may use an exponential average of the number of preceding image frames, such as described with respect to FIG. 9.

Figure 18:
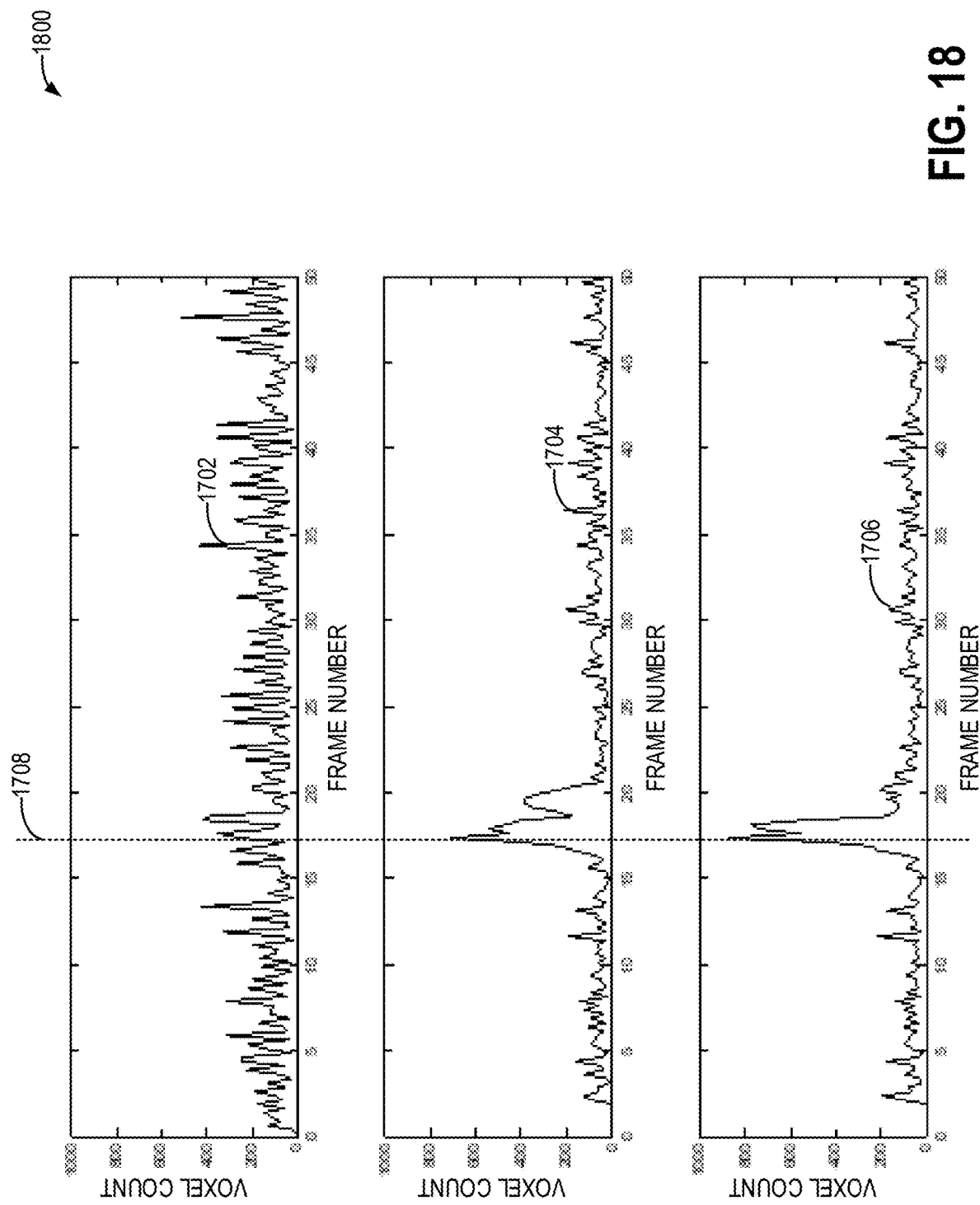
FIG. 18 shows a set of plots comparing patient motion tracking for the plurality of different voxel-wise methods over a second, shorter duration.

These differences are also shown in FIG. 18, which shows a set of motion plots 1800 that correspond to a shorter duration portion of the set of motion plots 1700 of FIG. 17. Thus, like elements are numbered the same and are not reintroduced. The set of motion plots 1800 further illustrates how the first method sensitively identifies frame-to-frame variation but not slower motions, as shown in the first plot 1702. In contrast, the second method and the third method sensitively identify the slower motion of the motion event 1708 but not the rapid cardiac motion, as illustrated in the second plot 1704 and the third plot 1706, respectively.

Turning now to FIG. 19, an exemplary frequency component analysis 1900 is shown for three components identified via PCA, such as the PCA described above with respect to FIG. 11. A frequency analysis of a first component is shown in a first FFT 1902, a second frequency analysis of a second component is shown in a second FFT 1904, and a third frequency analysis of a third component is shown in a third FFT 1906. For each FFT, the horizontal axis is the frequency (in Hz) and the vertical axis is the amplitude, as labeled.

The first FFT 1902 indicates a maximum amplitude at approximately 1.2 Hz, which corresponds to a cardiac component of the signal (1.2 Hz=72 beats per minute). Thus, the first component may be selected for evaluating cardiac motion. The second FFT 1904 and the third FFT 1906 both have a maximum amplitude around 0.3 Hz, which corresponds to a respiratory component of the signal. However, the maximum amplitude is greater for the second component than the third component, as shown by comparing the second FFT 1904 and the third FFT 1906 at 0.3 Hz. As such, the second component, and not the third component, may be selected for evaluating respiratory motion due to the stronger signal.

FIG. 20 shows exemplary physio waveforms 2000 that may be output based on the PCA of the real-time PET imaging data. A derived cardiac trace 2002 is shown relative to cardiac triggers 2004, which are shown as dashed circles (only one of which is labeled). Similarly, a derived respiratory trace 2006 is shown relative to respiratory triggers 2008. Each trace is shown as a change in signal (vertical axis) over time (horizontal axis). Positive values of the change in signal denote motion in a first direction, while negative values of the change in signal denote motion in a second, opposite direction. The cardiac triggers 2004 and the respiratory triggers 2008 are derived from external sensors used to measure a heartbeat and respiratory phase, respectively.

Each cardiac trigger 2004 corresponds to a spike in the derived cardiac trace 2002, indicating that the derived cardiac trace 2002 is able to accurately detect cardiac motion. As such, the PET data alone provides the same information as derived using external sensors, enabling "deviceless triggering" with reduced scan set-up time (e.g., no sensor placement is needed). In particular, the data reduction inherent in live reconstruction makes the cardiac trigger extraction more viable than by using sinogram creation and analysis. The respiratory trace 2006 similarly agrees with the respiratory triggers 2008. However, the respiratory trace 2006 detects a deep breath at around 18 seconds that did not generate a respiratory trigger 2008. As such, the PCA of the real-time PET imaging data may be able to detect changes in respiratory motion that is not identified by the external sensors due to, for example, gating algorithms associated with the external sensors. Thus, the respiratory trace 2006 enables detection of anomalous breathing patterns for a more accurate overview of patient breathing.

In this way, patient motion may be tracked in real-time in order to identify emission data obtained during periods of movement (e.g., when a magnitude of the patient motion exceeds a threshold, as determined via displacement and/or a per-voxel variation). As a result, various adjustments and adaptations to an imaging protocol may be made in real-time in order to compensate for the patient motion and/or exclude data obtained during the patient motion without negatively affecting image quality or scanner resources. By tracking the patient motion in real-time, diagnostic PET images may be generated with fewer motion artifacts, increasing a quality of the diagnostic PET images and a diagnostic accuracy of the diagnostic PET images. Further, by tracking the patient motion using PET image frames reconstructed using a fast reconstruction method that uses list-mode TOF data and does not employ scatter correction, attenuation correction, and motion correction, the PET image frames may be reconstructed live (e.g., as the data is acquired) while avoiding memory locks and reducing processing time. Overall, an occurrence of patient rescans may be decreased while a quantitative accuracy of the final PET images may be increased, reducing imaging costs and a time to diagnosis.

The technical effect of computing a series of PET image frames from image space using data acquired over a short time duration is that the series of PET image frames may be reconstructed in real-time, enabling live tracking of patient motion.

The technical effect of determining patient motion based on a per-voxel variation in live PET images is that patient motion may be quickly determined.

The technical effect of analyzing selected voxels having a greatest variation is that a signal-to-noise ratio of a detected motion signal is increased and a processing efficiency is increased.

An example provides a method for a medical imaging system, comprising acquiring emission data during a positron emission tomography (PET) scan of a patient; reconstructing a series of live PET images while acquiring the emission data; and tracking motion of the patient during the acquiring based on the series of live PET images.

In an example, reconstructing the series of live PET images while acquiring the emission data includes performing a list-mode reconstruction in real-time.

In examples, each live PET image in the series of live PET images is reconstructed from emission data acquired during a defined time duration. In some examples, reconstructing the series of live PET images while acquiring the emission data includes, for each live PET image in the series of live PET images: dividing the emission data acquired during the defined time duration into subsets; reconstructing an image iteration from each subset of the emission data; and combining the image iteration from every subset to produce the live PET image. In one example, reconstructing the image iteration from each subset of the emission data includes assigning the emission data within a given subset to a plurality of groups and processing each group in parallel. In another example, reconstructing the image iteration from each subset of the emission data includes determining a start position and a stop position for a TOF kernel within each line of response (LOR) in the given subset of the emission data; computing projection coefficients based on a path length and kernel height for each voxel traversed by the TOF kernel; and reconstructing the image iteration by forward and back projecting using the computed projection coefficients.

In examples, tracking the motion of the patient during the PET scan based on the series of live PET images includes performing image registration on each live PET image in the series of live PET images; determining variation of the patient between time points in the series of live PET images; and responsive to the variation exceeding a threshold, performing a motion response. As one example, performing the motion response includes at least one of outputting an alert, displaying a plot of the motion of the patient, extending an acquisition time for acquiring the emission data, segregating emission data acquired while the displacement is greater than the threshold from emission data acquired while the displacement is less than the threshold, and prompting use of a motion correction reconstruction technique for the emission data acquired while the displacement is greater than the threshold.

The method may further comprise reconstructing a non-live PET image after acquiring the emission data, wherein reconstructing the non-live PET image includes performing scatter correction and attenuation correction, and reconstructing the series of live PET images includes not performing the scatter correction and attenuation correction.

The method may further comprise reconstructing a non-live PET image after acquiring the emission data, wherein reconstructing the non-live PET image includes performing motion correction, and reconstructing the series of live PET images includes not performing the motion correction.

An example method for positron emission tomography (PET), comprises reconstructing image frames using emission data acquired in real-time while performing an emission scan of a patient; indicating patient motion in response to a displacement of the patient between image frames exceeding a threshold; and in response to the patient motion, performing one or more motion detection responses.

In an example, performing one or more motion detection responses includes: segregating emission data acquired during the indicated patient motion; and not using the segregated emission data during reconstruction of a final PET image of the patient.

In an example, performing one or more motion detection responses includes performing motion correction on only emission data acquired during and after the indicated patient motion during reconstruction of a final PET image of the patient.

In an example, performing one or more motion detection responses includes extending an acquisition time for performing the emission scan of the patient.

In examples, each image frame is reconstructed from emission data acquired during a determined time period of the emission scan, and reconstructing the image frames using the emission data acquired in real-time while performing the emission scan of the patient includes, for each image frame: determining projections from the emission data acquired during the determined time period as soon as the determined time period is complete; and reconstructing the image frame from the determined projections.

An example system comprises a detector array configured to acquire emission data during a scan of a subject; and a processor operationally coupled to the detector array storing executable instructions in non-transitory memory that, when executed, cause the processor to: track motion of the subject in real-time during the scan based on the acquired emission data; and adjust parameters of the scan responsive to the motion of the subject exceeding a threshold. In examples, to track the motion of the subject in real-time during the scan based on the acquired emission data, the processor includes additional executable instructions in non-transitory memory that, when executed, cause the processor to: reconstruct images of the subject at pre-determined time points, each time point separated by a defined interval and each image reconstructed from emission data acquired during the immediately preceding interval; and compare a current image of the subject with a previous image to determine a magnitude of the motion of the subject between the previous image and the current image. In one example, to reconstruct the images of the subject, the processor includes additional executable instructions in non-transitory memory that, when executed, cause the processor to: perform parallel processing of subsetted emission data determined from the emission data acquired during the immediately preceding interval; determine projections from the subsetted emission data; and reconstruct the current image from the determined projections.

In an example, to adjust the parameters of the scan responsive to the motion of the subject exceeding the threshold, the processor includes additional executable instructions in non-transitory memory that, when executed, cause the processor to: extend a duration of the scan; and output a motion detection alert.

In an example, to adjust the parameters of the scan responsive to the motion of the subject exceeding the threshold, the processor includes additional executable instructions in non-transitory memory that, when executed, cause the processor to: separate emission data acquired while the motion of the subject exceeds the threshold from emission data acquired while the motion of the subject does not exceed the threshold; and reconstruct a diagnostic image of the subject using only the emission data acquired while the motion of the subject does not exceed the threshold.

The disclosure also provides support for a method for a medical imaging system, comprising: acquiring emission data during a positron emission tomography (PET) scan of a patient, reconstructing a series of live PET images while acquiring the emission data, tracking motion of the patient during the acquiring by determining a per-voxel variation for selected voxels in a current live PET image of the series of live PET images, and outputting an indication of patient motion based on the per-voxel variation for the selected voxels in each live PET image. In a first example of the method, reconstructing the series of live PET images while acquiring the emission data includes performing a list-mode reconstruction in real-time without performing scatter correction and attenuation correction, and the method further comprises: reconstructing a non-live PET image after acquiring the emission data, including performing the scatter correction and the attenuation correction. In a second example of the method, optionally including the first example, tracking the motion of the patient during the acquiring by determining the per-voxel variation for the selected voxels in the current live PET image of the series of live PET images comprises: generating a mean image of a quiescent period during the acquiring, generating a weighting image of the quiescent period, and determining the per-voxel variation for the selected voxels in the current live PET image by using the mean image and the weighting image to remove a background noise. In a third example of the method, optionally including one or both of the first and second examples, determining the per-voxel variation for the selected voxels in the current live PET image by using the mean image and the weighting image to remove the background noise comprises, for each voxel: determining a difference between a voxel value of the current live PET image and a mean value of a corresponding voxel of the mean image, and scaling the difference by the weighting image. In a fourth example of the method, optionally including one or more or each of the first through third examples, tracking the motion of the patient during the acquiring by determining the per-voxel variation for the selected voxels in the current live PET image of the series of live PET images comprises: determining a difference in a voxel value between two adjacent live PET images for each voxel, and dividing the difference by a square root sum of the voxel value of the two adjacent live PET images for each voxel. In a fifth example of the method, optionally including one or more or each of the first through fourth examples, tracking the motion of the patient during the acquiring by determining the per-voxel variation for the selected voxels in the current live PET image of the series of live PET images comprises, for each voxel: determining a background noise reference as a rolling mean of a number of image frames, determining a difference in a voxel value between the current live PET image and the background noise reference, and dividing the difference by the background noise reference. In a sixth example of the method, optionally including one or more or each of the first through fifth examples, the rolling mean is one of a boxcar average, an exponential average, a time-weighted average, and a local average. In a seventh example of the method, optionally including one or more or each of the first through sixth examples, tracking the motion of the patient during the acquiring by determining the per-voxel variation for the selected voxels in the current live PET image of the series of live PET images comprises: performing a principal component analysis on the selected voxels in the series of live PET images, and performing a frequency analysis on a number of components identified by the principal component analysis to identify components with frequencies of interest. In an eighth example of the method, optionally including one or more or each of the first through seventh examples, outputting the indication of patient motion based on the per-voxel variation for the selected voxels in the current live PET image comprises outputting the patient motion as a change in a magnitude of the components with the frequencies of interest over time. In a ninth example of the method, optionally including one or more or each of the first through eighth examples, outputting the indication of patient motion based on the per-voxel variation for the selected voxels in the current live PET image comprises displaying voxels having a determined variation that is greater than a threshold variation as a colorized overlay on the current live PET image of the series of live PET image. In a tenth example of the method, optionally including one or more or each of the first through ninth examples, outputting the indication of patient motion based on the per-voxel variation for the selected voxels in the current live PET image comprises displaying a color map of z-scores for each voxel. In an eleventh example of the method, optionally including one or more or each of the first through tenth examples, outputting the indication of patient motion based on the per-voxel variation for the selected voxels in the current live PET image comprises displaying a motion plot generated from the per-voxel variation for each PET image of the series of live PET images.

The disclosure also provides support for a method for positron emission tomography (PET), comprising: acquiring emission data while performing an emission scan of a patient, reconstructing real-time image frames during the emission scan using the emission data as the emission data is acquired, determining a motion of the patient in the real-time image frames based on a per-voxel variation relative to a reference, indicating patient motion in response to a number of voxels having a greater than threshold per-voxel variation exceeding a motion threshold, and not using the emission data acquired while the number of voxels having the greater than threshold per-voxel variation exceeds the motion threshold during reconstruction of a final PET image of the patient after the emission scan. In a first example of the method, the reference comprises each of a mean image generated from a number of real-time image frames acquired during a quiescent period of the emission scan of the patient and a standard deviation image generated from the number of real-time image frames acquired during the quiescent period of the emission scan. In a second example of the method, optionally including the first example, the reference comprises an immediately preceding real-time image frame. In a third example of the method, optionally including one or both of the first and second examples, the reference comprises a rolling mean of a number of preceding real-time image frames. In a fourth example of the method, optionally including one or more or each of the first through third examples, the reference is determined via a principal component analysis of a number of preceding real-time image frames.

The disclosure also provides support for a system, comprising: a detector array configured to acquire emission data during a scan of a subject, and a controller operationally coupled to the detector array storing executable instructions in non-transitory memory that, when executed, cause the controller to: reconstruct live images of the subject at pre-determined time points during the scan of the subject based on acquired emission data, and track a motion of the subject in real-time during the scan based on a voxel-wise variation between image frames of the live images. In a first example of the system, to track the motion of the subject in real-time during the scan based on the voxel-wise variation between the image frames of the live images, includes additional executable instructions stored in the non-transitory memory that, when executed, cause the controller to: determine a voxel-wise background noise of the scan of the subject, determine the voxel-wise variation between the image frames relative to the voxel-wise background noise, and output a real-time indication of the motion of the subject as one or more of a map indicating a magnitude of the voxel-wise variation at each voxel of the live images, a motion overlay on the live images, and a plot of a number of voxels having voxel-wise variations that exceed a threshold variation per image frame of the live images. In a second example of the system, optionally including the first example, the controller includes additional executable instructions stored in the non-transitory memory that, when executed, cause the controller to: adjust parameters of the scan responsive to the motion of the subject exceeding a threshold motion, and after the scan of the subject, reconstruct a diagnostic image of the subject.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a medical imaging system, comprising: acquiring emission data during a positron emission tomography (PET) scan of a patient;
reconstructing a series of live PET images while acquiring the emission data;
tracking motion of the patient during the acquiring by determining a per-voxel variation for selected voxels in a current live PET image of the series of live PET images; and
outputting an indication of patient motion based on the per-voxel variation for the selected voxels in each live PET image,
wherein tracking the motion of the patient during the acquiring by determining the per-voxel variation for the selected voxels in the current live PET image of the series of live PET images comprises:
generating a mean image of a quiescent period during the acquiring;
generating a weighting image of the quiescent period; and
determining the per-voxel variation for the selected voxels in the current live PET image by using the mean image and the weighting image to remove a background noise.

2. The method of claim 1, wherein reconstructing the series of live PET images while acquiring the emission data includes performing a list-mode reconstruction in real-time without performing scatter correction and attenuation correction, and the method further comprises:
reconstructing a non-live PET image after acquiring the emission data, including performing the scatter correction and the attenuation correction.

3. The method of claim 1, wherein determining the per-voxel variation for the selected voxels in the current live PET image by using the mean image and the weighting image to remove the background noise comprises, for each voxel:
determining a difference between a voxel value of the current live PET image and a mean value of a corresponding voxel of the mean image; and
scaling the difference by the weighting image.

4. The method of claim 1, wherein tracking the motion of the patient during the acquiring by determining the per-voxel variation for the selected voxels in the current live PET image of the series of live PET images comprises:
determining a difference in a voxel value between two adjacent live PET images for each voxel; and
dividing the difference by a square root sum of the voxel value of the two adjacent live PET images for each voxel.

5. The method of claim 1, wherein tracking the motion of the patient during the acquiring by determining the per-voxel variation for the selected voxels in the current live PET image of the series of live PET images comprises, for each voxel:
determining a background noise reference as a rolling mean of a number of image frames;
determining a difference in a voxel value between the current live PET image and the background noise reference; and
dividing the difference by the background noise reference.

6. The method of claim 5, wherein the rolling mean is one of a boxcar average, an exponential average, a time-weighted average, and a local average.

7. The method of claim 1, wherein tracking the motion of the patient during the acquiring by determining the per-voxel variation for the selected voxels in the current live PET image of the series of live PET images comprises:
performing a principal component analysis on the selected voxels in the series of live PET images; and performing a frequency analysis on a number of components identified by the principal component analysis to identify components with frequencies of interest.

8. The method of claim 7, wherein outputting the indication of patient motion based on the per-voxel variation for the selected voxels in the current live PET image comprises outputting the patient motion as a change in a magnitude of the components with the frequencies of interest over time.

9. The method of claim 1, wherein outputting the indication of patient motion based on the per-voxel variation for the selected voxels in the current live PET image comprises displaying voxels having a determined variation that is greater than a threshold variation as a colorized overlay on the current live PET image of the series of live PET image.

10. The method of claim 1, wherein outputting the indication of patient motion based on the per-voxel variation for the selected voxels in the current live PET image comprises displaying a color map of z-scores for each voxel.

11. The method of claim 1, wherein outputting the indication of patient motion based on the per-voxel variation for the selected voxels in the current live PET image comprises displaying a motion plot generated from the per-voxel variation for each PET image of the series of live PET images.

12. A method for positron emission tomography (PET), comprising:
acquiring emission data while performing an emission scan of a patient;
reconstructing real-time image frames during the emission scan using the emission data as the emission data is acquired;
determining a motion of the patient in the real-time image frames based on a per-voxel variation relative to a reference;
indicating patient motion in response to a number of voxels having a greater than threshold per-voxel variation exceeding a motion threshold; and
not using the emission data acquired while the number of voxels having the greater than threshold per-voxel variation exceeds the motion threshold during reconstruction of a final PET image of the patient after the emission scan.

13. The method of claim 12, wherein the reference comprises each of a mean image generated from a number of real-time image frames acquired during a quiescent period of the emission scan of the patient and a standard deviation image generated from the number of real-time image frames acquired during the quiescent period of the emission scan.

14. The method of claim 12, wherein the reference comprises an immediately preceding real-time image frame.

15. The method of claim 12, wherein the reference comprises a rolling mean of a number of preceding real-time image frames.

16. The method of claim 12, wherein the reference is determined via a principal component analysis of a number of preceding real-time image frames.

17. A system, comprising:
a detector array configured to acquire emission data during a scan of a subject; and
a controller operationally coupled to the detector array storing executable instructions in non-transitory memory that, when executed, cause the controller to:
reconstruct live images of the subject at pre-determined time points during the scan of the subject based on acquired emission data; and
track a motion of the subject in real-time during the scan based on a voxel-wise variation between image frames of the live images,
wherein to track the motion of the subject in real-time during the scan based on the voxel-wise variation between the image frames of the live images, includes additional executable instructions stored in the non-transitory memory that, when executed, cause the controller to:
determine a voxel-wise background noise of the scan of the subject;
determine the voxel-wise variation between the image frames relative to the voxel-wise background noise; and
output a real-time indication of the motion of the subject as one or more of a map indicating a magnitude of the voxel-wise variation at each voxel of the live images, a motion overlay on the live images, and a plot of a number of voxels having voxel-wise variations that exceed a threshold variation per image frame of the live images.

18. The system of claim 17, wherein the controller includes additional executable instructions stored in the non-transitory memory that, when executed, cause the controller to:
adjust parameters of the scan responsive to the motion of the subject exceeding a threshold motion; and
after the scan of the subject, reconstruct a diagnostic image of the subject.

* * * * *